US012799453B2

(12) United States Patent
Rawadi et al.

(10) Patent No.: US 12,799,453 B2
(45) Date of Patent: Nov. 17, 2026

(54) **BACTERIAL STRAIN BELONGING TO THE GENUS *CHRISTENSENELLA*, AND COMPOSITIONS**

(71) Applicant: VERB BIOTICS, Boston, MA (US)

(72) Inventors: Georges Rawadi, Paris (FR); Sandrine Paule Claus, Bordeaux (FR); Ccori Silbina Martinez Tuppia, Pessac (FR); Katy Nicole Le Corf, Merignac (FR); Wilfrid Bernard Philippe Mazier, Bordeaux (FR); Marion Sophie Madeleine Soto, Merignac (FR); Frédéric Elustondo, Bordeaux (FR)

(73) Assignee: VERB BIOTICS, Boston, MA (US)

( * ) Notice: Subject to any disclaimer, the term of this patent is extended or adjusted under 35 U.S.C. 154(b) by 600 days.

(21) Appl. No.: 18/269,878

(22) PCT Filed: Sep. 16, 2021

(86) PCT No.: PCT/EP2021/075475
§ 371 (c)(1),
(2) Date: Jul. 6, 2023

(87) PCT Pub. No.: WO2022/058423
PCT Pub. Date: Mar. 24, 2022

(65) Prior Publication Data

US 2024/0318130 A1 Sep. 26, 2024

(30) Foreign Application Priority Data

Sep. 16, 2020 (FR) ....................................... 2009377

(51) Int. Cl.

| | |
|---|---|
| ***C12N 1/205*** | (2026.01) |
| ***A61K 35/741*** | (2015.01) |
| ***A61P 1/16*** | (2006.01) |
| ***A61P 3/04*** | (2006.01) |
| ***A61P 29/00*** | (2006.01) |
| ***C12R 1/145*** | (2006.01) |

(52) U.S. Cl.
CPC ............ *C12N 1/205* (2021.05); *A61K 35/741* (2013.01); *A61P 1/16* (2018.01); *A61P 3/04* (2018.01); *A61P 29/00* (2018.01); *C12R 2001/145* (2021.05)

(58) Field of Classification Search
None
See application file for complete search history.

(56) References Cited

U.S. PATENT DOCUMENTS

| | | | | |
|---|---|---|---|---|
| 2019/0282633 | A1* | 9/2019 | Zou ........................ | C12N 1/205 |
| 2022/0000942 | A1 | 1/2022 | Gerranz et al. | |
| 2023/0167401 | A1 | 6/2023 | Rawadi et al. | |

FOREIGN PATENT DOCUMENTS

| | | | |
|---|---|---|---|
| WO | WO 2015164555 | A1 | 10/2015 |
| WO | WO 2019032573 | A1 | 2/2019 |
| WO | WO 2020109414 | A1 | 6/2020 |
| WO | WO 2020182916 | A1 | 9/2020 |

OTHER PUBLICATIONS

Waters, J., et al., "The human gut bacteria Christensenellaceae are widespread, heritable, and associated with health", BMC Biology, Oct. 28, 2019, pp. 1-11, vol. 17, No. 1.
Morotomi, M., et al., "Description of *Christensenella minuta* gen. nov., sp. nov., isolated from human faeces, which forms a distinct branch in the order Clostridiales, and proposal of *Christensenellaceae* fam. nov.", International Journal of Systematic and Evolutionary Microbiology, Feb. 25, 2011, pp. 144-149.
Chang, C., et al., "Next generation probiotics in disease amelioration", Journal of Food and Drug Analysis,, Jul. 1, 2019, pp. 615-622, vol. 27, No. 3.
Goodrich, J., et al., "Human Genetics Shape the Gut Microbiome", Cell, Elsevier, Amsterdam NL, Nov. 6, 2014, pp. 789-799, vol. 159, No. 4.
Peters, R., et al, "A taxonomic signature of obesity in a large study of American adults", Scientific Reports, Dec. 1, 2018, pp. 1-13, vol. 8, No. 101.
Mazier W., et al., "A New Strain of Christensenella minuta as a Potential Biotherapy for Obesity and Associated Metabolic Diseases", CELLS, Apr. 6, 2021, pp. 1-17, vol. 10, No. 4.

* cited by examiner

*Primary Examiner* — Brian Gangle
(74) *Attorney, Agent, or Firm* — Greer, Burns & Crain, Ltd.

(57) ABSTRACT

The present invention relates to a bacterial strain belonging to the genus *Christensenella* and the bacteria derived therefrom, a composition comprising said strain or bacteria, and its uses in particular in the treatment and/or prevention of diseases such as obesity, metabolic diseases, inflammatory bowel diseases, cancers, and diseases associated with dysbiosis of the microbiota.

12 Claims, 11 Drawing Sheets

Specification includes a Sequence Listing.

BACTERIAL STRAIN BELONGING TO THE GENUS *CHRISTENSENELLA*, AND COMPOSITIONS

CROSS-REFERENCE TO RELATED APPLICATIONS

This application is a U.S. National Stage Application of PCT/EP2021/075475 filed Sep. 16, 2021, claiming the benefit of priority from French patent application FR2009377 filed Sep. 16, 2020, the entire disclosure of both applications is herein incorporated by reference.

TECHNICAL FIELD

The invention relates to a new bacterial strain belonging to the genus *Christensenella*, a composition comprising it and its uses, in particular as a medicament in the treatment and/or prevention of diseases such as metabolic diseases, inflammatory diseases, cancers or diseases associated with dysbiosis of the microbiota.

PRIOR ART

Our intestinal microbiota or "intestinal flora" consists of a set of non-pathogenic bacteria, viruses, parasites and fungi, or $10^{12}$ to $10^{14}$ microorganisms present in the digestive tract of each individual, which is 2 to 10 times more than the number of cells in our body. Therefore, its role has been increasingly studied in recent years. In 2012, a microbiologist identified and cultivated from human faeces a new species: *Christensenella minuta*, belonging to gram-negative Clostridia. (Morotomi et al., Description of *Christensenella minuta* gen. nov., sp. nov., isolated from human faeces, which forms a distinct branch in the order Clostridiales, and proposal of Christensenellaceae fam. nov., International Journal of Systematic and Evolutionary Microbiology (2012), 62, 144-149).

In 2014, Goodrich et al. identified *Christensenella minuta* as the most hereditary bacterial taxon in humans and also suggested its therapeutic potential.

To date, it is accepted by the scientific community that the human intestinal microbiota is linked to the appearance of certain "non-transmissible" pathologies associated with dysbiosis of the microbiota, such as obesity, diabetes, metabolic diseases, intestinal inflammatory diseases, or even depression. However, the prevalence of these diseases does not cease to increase, without any satisfactory treatment.

On the global scale, the number of obesity cases has almost tripled since 1975. Thus, 39% of adults are considered overweight and 13% suffer from obesity. The associated complications are well known and include metabolic diseases, in particular type 2 diabetes, of which 44% of cases are attributable to excess weight/obesity, cardiac diseases of which 23% of cases are attributable to excess weight/obesity, cancers which represent between 7% and 41% of the cases attributable to excess weight/obesity and intestinal inflammatory diseases. Excess weight/obesity thus leads to the death of at least 2.8 million people each year, which makes it the fifth cause of mortality according to the WHO.

Despite progress in understanding and supporting patients, modern medicine does not have a satisfactory solution, which causes major public health problems. Previously confined to high-income countries, obesity is now present in low-income or medium-income countries.

The drug treatments are very limited and the surgical treatments are reserved for the most severe forms associated with complications and lead to serious constraints for the patient.

The microbial ecology has thus been increasingly studied in recent years as a regulator of metabolic functions of the host and its central role in establishing a healthy ecosystem.

Certain bacteria of the genus *Christensenella* have been associated with a low body mass index in numerous human cohorts and other studies have suggested a protective role in regulating inflammation.

An absence or deficiency of the bacteria of genus *Christensenella* is reported to be particularly involved in obesity, metabolic diseases, cardiac and vascular diseases, liver and bile duct diseases, kidney diseases, joint diseases associated with excess weight, cancers and in particular cancers linked to metabolism and/or dysbiosis of the microbiota, autoimmune diseases, atopic dermatitis, chronic inflammatory bowel diseases, pneumonia, infectious diarrhoea, food allergies, inflammatory kidney conditions and neurological disorders, for example degenerative diseases or neuropsychiatric diseases such as anxiety-related disorders or eating disorders (for example bulimia).

However, no satisfactory solution is available to patients at present.

There is therefore a strong medical need for a product capable of acting on the intestinal microbiota, in particular on the dysbiosis of the intestinal microbiota in order to prevent and/or treat diseases associated with dysbiosis of the intestinal microbiota.

An objective of the present invention is therefore to provide a solution that is simple, effective and economical for restoring healthy intestinal microbiota, treating dysbiosis of the microbiota and reducing the prevalence in the world of diseases associated with an imbalance of the intestinal microbiota, such as obesity/excess weight, inflammatory diseases, metabolic diseases and cancers, and other diseases associated with dysbiosis of the intestinal microbiota.

SUMMARY OF THE INVENTION

To meet this objective, the invention proposes a new bacterial strain of specific *Christensenella minuta* deposited with the Institut Leibniz DSMZ (Deutsche Sammlung von Mikroorganismen und Zellkulturen GmbH, or German is Collection of Microorganisms and Cell Cultures GmbH) under number DSM 33407.

Among the multitude of bacteria present in the intestinal microbiota, the inventors were able to identify this bacterial strain of specific *Christensenella minuta* particularly suitable for the prevention and/or treatment of "non-transmissible" pathologies associated with dysbiosis of the intestinal 2 microbiota, in particular diseases such as obesity and metabolic diseases, inflammatory diseases, cancers, and others which will be detailed in the following description.

Thus, the invention relates to a bacterial strain of *Christensenella minuta* deposited under number DSM 33407, having the 16S rDNA sequence, the sequence SEQ ID NO:1, thus all strains comprising a nucleotide sequence having at least 99.90% ANI (Average Nucleotide Identity) with the nucleotide sequence of the genome of the bacterial strain DSM 33407.

The invention also targets the culture supernatant of the bacterial strain according to the invention and/or of a derived strain.

The invention also relates to a composition comprising at least said bacterial strain according to the invention and/or the culture supernatant, in a physiologically acceptable medium.

Finally, the invention is particularly suitable for using said bacterial strain, said supernatant or said composition according to the invention as a medicament, in particular in the prevention and/or treatment of dysbiosis of the microbiota or diseases associated with dysbiosis of the intestinal microbiota.

Preferentially, the invention aims to prevent and/or treat obesity and metabolic diseases, and/or chronic inflammatory bowel diseases.

Finally, the invention also relates to a non-therapeutic use of the bacterial strain according to the invention, and/or of the supernatant according to the invention, and/or of the composition according to the invention for maintaining and/or reinforcing the intestinal microbiota and/or supporting the diversity of the intestinal microbiota and/or promoting the increase of beneficial bacteria in the intestinal microbiota in a healthy subject.

Other features and advantages will emerge from the detailed description of the invention, examples and figures that follows.

DETAILED DESCRIPTION OF THE INVENTION

Definition

Figure 1:
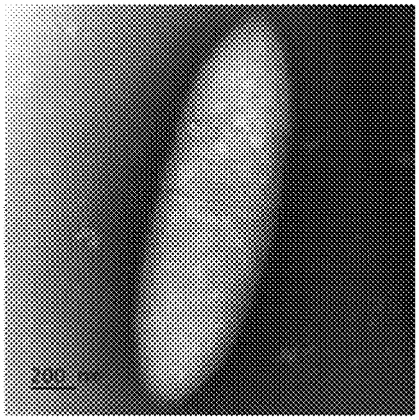
FIG. 1 is an image of a bacterium *Christensenella minuta* according to the invention corresponding to the DSM 33407 strain produced by transmission electron microscopy in negative colouring (magnification: 36k×).

The term "bacterium" in the sense of the invention is understood to mean a single-cell microorganism capable of being reproduced by cell division. The bacteria are classified by family, genus, species. Each bacterial species comprises a diversity of bacterial strains. The bacterial strain according to the invention belongs to the family Christensenellaceae, the genus *Christensenella* and the species *minuta*. Therefore, "bacterial strain" or "strain" within the meaning of the invention is a specific bacterial strain but also all the bacteria derived from the strain or obtained from the strain or corresponding to the bacterial strain and having the same metabolic functions, for example at least one bacterium removed from a colony derived from the strain. For the purposes of the invention, "bacterium (bacteria) according to the invention" is a bacterial strain according to the invention.

"Derived bacterial strain" or "mutant strain" or "derived strain" or "derived bacteria" within the meaning of the invention is understood to mean a bacterial strain having a strong similarity with the bacterial strain deposited under the number DSM 33407. Preferentially, the strain comprises a nucleotide sequence having at least 99.90% ANI identity with the nucleotide sequence of the genome of the bacterial strain DSM 33407, more preferentially at least 99.91%, at least 99.92%, at least 99.93%, at least 99.94%, at least 99.95%, at least 99.96%, at least 99.97%, at least 99.98%, or at least 99.99% ANI identity.

The term "supernatant" within the meaning of the invention is understood to mean the culture supernatant of the bacterial strain according to the invention or of the derived strain optionally comprising cell compounds and/or debris of said strain, and/or metabolites and/or molecules secreted by said strain.

"Prevention" within the meaning of the invention is understood to mean the reduction to a lesser degree of the risk or the probability of occurrence of a given phenomenon, that is, in the context of the present invention, dysbiosis of the intestinal microbiota and associated diseases, for example obesity.

"Treatment" within the meaning of the invention is understood to mean a decrease in the progression of the disease, a stabilization, an inversion or regression, or even an interruption or inhibition of the progression of dysbiosis of the intestinal microbiota, and/or of a disease such as a metabolic disease, for example obesity, or an inflammatory disease or cancer. In the context of the invention, these terms also apply to one or more symptoms of said diseases of the present invention.

The term "subject" within the meaning of the invention is preferentially understood to mean a human subject or non-human animal.

For the purposes of the invention, the term "physiologically acceptable medium" refers to a medium which is compatible with the body of the individual to which said composition is to be administered. It may involve, for example, a non-toxic solvent such as water. In particular, said medium is compatible with oral administration.

For the purposes of the invention, the term "pharmaceutically acceptable excipient" is intended to mean any compound making it possible to facilitate the formulation of the composition and not modifying the nature of the biological activity of the active ingredient. A pharmaceutically acceptable excipient may be a solvent, plasticiser, lubricant, dispersion medium, absorption-retarding agents, flow agent, etc.

The term "disease associated with dysbiosis of the intestinal microbiota" within the meaning of the invention is understood to mean diseases associated with dysbiosis of the intestinal microbiota such as certain metabolic diseases, for example obesity-related diseases including obesity, diabetes, NASH, hepatic or pancreatic steatosis, inflammatory diseases such as chronic inflammatory bowel diseases, for example Crohn's disease, gastric diseases, pancreatic diseases, or irritable bowel syndrome, chronic diseases associated with dysbiosis, cardiac and vascular diseases, cancers, for example cancers linked to metabolism.

Bacterial Strain or Supernatant According to the Invention

The present invention therefore relates to a bacterial strain of *Christensenella minuta* deposited under number DSM 33407, referred to below as strain DSM 33407 or strain according to the invention or bacterial strain according to the invention.

The inventors have discovered a bacterial strain of *Christensenella minuta* deposited under the number DSM 33407 and isolated from faeces of a healthy human donor. The inventors have thus demonstrated in preclinical obesity models that the administration of such a strain makes it possible to prevent weight gain and associated metabolic diseases, including in the context of a calorie-ich diet Surprisingly, a persistent effect of the treatment on the loss of weight was demonstrated after the treatment has stopped and in the context of a calorie-rich diet.

The inventors have also demonstrated in various models that the bacterial strain DSM 33407 makes it possible to:

- limit the compulsive food behaviours suggesting an anorexigenic effect,
- inhibit hepatic glycolysis and thus act on hepatic metabolism and therefore prevent the accumulation of lipids,
- obtain a peripheral immunomodulatory and anti-inflammatory effect and thus prevent and treat inflammatory diseases,
- obtain a protective effect of the liver function for preventing or treating liver diseases such as NASH (metabolic steatohepatitis) or cirrhosis,
- restore the bile acid balance and thus prevent and/or treat diseases associated with a disorder for the production of bile such as biliary lithiases and other bile duct pathologies such as primary sclerosing cholangitis,
- obtain an anti-proliferative effect suggesting an effect in the prevention and treatment of cancers,
- promote beneficial bacteria to the microbiota such as Ruminococcaceae and Bifidobacteriaceae and maintain the diversity of the intestinal microbiota.

This bacterial strain of *Christensenella minuta* was thus deposited with the Leibniz Institute DSMZ (Deutsche Sammlung von Mikroorganismen und Zellkulturen GmbH, meaning "German Collection of Microorganisms and Cell Cultures GmbH") under number DSM 33407 on 09/09/2020. Said strain has a 16S rDNA sequence, the sequence SEQ ID NO:1. In addition, a person skilled in the art by their general knowledge is able to determine the complete sequence of is the genome of the bacterium according to the invention from the strain deposited and accessible from the DSMZ under the number DSM 33407.

The scientific classification of the DSM 33407 bacterial strain is as follows: Domain: Bacteria; Phylum: Firmicutes; Class: Clostridia; Order: Clostrdiales; Family: Chnistensenellaceae; Genus: *Christensenella*; Species: *C. minuta.*

Another subject matter of the invention relates to a bacterial strain of *Christensenella minuta* derived from the bacterial strain deposited under the number DSM 33407. Said strain maintains or improves the capacities described within the scope of the present invention. Said derived strain can thus be produced naturally or intentionally by mutagenesis methods known in the prior art. By way of example, the mutagenesis methods that can be implemented within the scope of the present invention are the growth of the original microorganism in the presence of mutagenic or stress-producing agents, or by genetic engineering aiming to modify specific or non-specific genes such as directed mutagenesis or random mutagenesis. According to a preferred embodiment, the strain derived from the DSM 33407 strain of *C. minuta* is a genetically modified mutant.

Preferably, said derived strain comprises a 16S rRNA sequence having at least 99% identity with the 16S rRNA sequence of the bacterial strain DSM 33407.

16S ribosomal RNA (16S rRNA) is ribosomal RNA constituting the small subunit of prokaryotic ribosomes. The genes coding for this RNA are called 16S rDNA. The 16S rRNA or 16S rDNA sequence is very widely used in phylogenesis due to its very conserved structure, which makes it possible to reconstruct the evolutionary history of organisms and in particular of prokaryotes and bacteria.

The percentage of identity of the 16S rDNA sequence between two bacterial strains, more particularly between two strains of *C. minuta*, can be determined by the so-called BLAST method, which is a heuristic research method well known to a person skilled in the art. It makes it possible to find similar regions between two or more nucleotide or amino acid sequences, and to carry out an alignment of these homologous regions.

However, the 16S rDNA sequence does not always allow differentiation is of two strains of the same species having different properties, for example anti-inflammatory properties. Therefore, a person skilled in the art by their general knowledge is able to characterise a bacterial strain according to other parameters such as the calculation of phylogenetic distance based on the complete genome (ANI), the size of the genome, the CDS number (Coding DNA Sequence), but also the identification of genes specific to said strain of interest.

For the purposes of the invention, "ANI" refers to the percentage of average identity of the nucleotides calculated from the two-by-two comparison of all the genome sequences between the two bacterial strains. According to the general knowledge well known to a person skilled in the art, the genomic DNA can be extracted from said strain of interest deposited with the DSMZ from a pure bacterial culture from said strain of interest, followed by DNA sequencing according to various well-known methods, for example Sanger, Roche 454, Illumina, Oxford Nanopore and then the sequenced genome is assembled by biocomputing and the sequences obtained are analysed. Finally, the genomes of interest are compared two by two to calculate the ANI.

According to one variant, the invention also relates to a bacterial strain derived from *Christensenella minuta*, characterised in that it comprises a nucleotide sequence having at least 99.90% ANI identity with the nucleotide sequence of the bacterial strain DSM 33407.

Preferably, said strain according to the invention comprises a nucleotide sequence having at least 99.91%, at least 99.92%, at least 99.93%, at least 99.94%, at least 99.95%, at least 99.96%, at least 99.97%, at least 99.98%, at least 99.99% ANI identity with the nucleotide sequence of the bacterial strain DSM 33407.

Such a strain is therefore a bacterial strain of *Christensenella minuta* derived from the bacterial strain deposited under the number DSM 33407 making it possible to maintain or improve the described capacities of the DSM 33407 strain in the context of the present invention.

Said derived strain can thus be produced naturally or intentionally by mutagenesis methods known in the prior art.

According to one embodiment, the bacterial strain DSM 33407 and/or the strain derived therefrom can be used in any form producing the expected effects and the efficiency described in the present application. In particular, the strain can be in living (cultivable or not), dead, semi-live, attenuated or inactivated form. The dead, semi-living, attenuated or inactivated form can be obtained by various techniques known to a person skilled in the art. Mention will be made, for example, of the 2 following techniques: irradiation, thermal inactivation or freeze-drying, in particular by heat, exposure to an appropriate pH, UV, gamma rays, X-rays or high pressure.

The term "semi-active" thus denotes a bacterium with a low physiological activity whose ability to proliferate is reduced, temporarily or definitively. The term "inactivated" refers to a bacterium which is no longer capable, temporarily or definitively, of proliferating. The term "dead" refers to a bacterium that is definitively no longer capable of proliferating. The dead or inactivated bacteria can have intact or broken cell membranes. Thus, the term "inactivated" also refers to the obtained extracts and lysates of bacteria.

Another subject matter of the invention relates to the culture supernatant obtained from the bacterial strain DSM 33407 and/or the derived strain. Preferably, the culture supernatant comprises and at least one of the constituents selected from a bacterial cell compound, a bacterial cell debris, a metabolite and/or molecule(s) secreted by the strain and/or the derived strain, or combinations thereof.

Thus, the cell compounds and/or cell debris may be components of the wall, nucleic acids, membrane components, proteins, lipids, etc. The secreted metabolites or molecules may be any molecule produced or modified by the bacterium due to its metabolic activity during its growth, its use in technological processes (for example, but not limited thereto, methods for producing food or medicaments). By way of example, the metabolites or molecules may be proteins, amino acids, enzymes, lipids, nucleic acids, etc. "Metabolite and/or molecule(s) secreted by the strain and/or the derived strain" means a molecule produced and exported or released outside the bacterium by the bacterium.

Composition According to the Invention

The strain(s) according to the invention or derived strain (s) and/or the culture supernatant described previously and the bacteria derived from said strains are advantageously administered in a composition. Said composition comprises at least the strain(s), the useful bacterium (bacteria) and/or their supernatant in a physiologically acceptable medium.

Thus, another aspect of the invention relates to a composition comprising at least one bacterial strain deposited under the number DSM 33407 and/or at least one bacterial strain derived from the bacterial strain deposited under the number DSM 33407, and/or at least one culture supernatant obtained from the DSM 33407 strain and/or the derived strain, hereinafter referred to as the composition according to the invention.

Preferably, the composition according to the invention comprises a physiologically acceptable medium.

According to a preferred embodiment, the composition according to the invention further comprises at least one additional compound. An additional compound may be an ingredient, a molecule, an active principle, a microorganism, a bacterium or a mixture of bacteria.

Preferably, the additional compound is a microorganism different from the bacterial strain according to the invention or from the derived strain. More preferably, the microorganism is a bacterium of the genus *Christensenella*. As an example, mention may be made of a bacterium belonging to the species *C. minuta, C. timonensis, C. massiliensis* and mixtures thereof.

According to one variant, the additional compound is a probiotic and/or a prebiotic. The prebiotic may be, for example, at least one prebiotic selected from galactooligosaccharides, fructooligosaccharides, inulins, arabinoxylans, beta-glucans, lactoglobulins and/or beta-caseins.

According to another variant, the additional compound can be:

- at least one bacterium producing lactic acid that makes it possible to create an anaerobic environment favourable to Christensenellaceae such that at least one bacterium selected from the bacteria of the genus *Lactobacillus* spp., *Bifidobacterium* spp., *Streptococcus* spp. and/or
- at least one bacterium producing butyric acid that makes it possible to create an environment favourable to Christensenellaceae such as a bacterium of the genus Ruminococcaceae,
- at least one other organism promoting the anaerobic conditions required for survival of the Chistensenellaceae such that at least one yeast selected from among *Saccharomyces* spp. or microorganisms of the Metanobacteiaceae family, and/or
- at least one bacterium associated with the ecosystem of the Chrstensenellaceae since they facilitate their survival in the intestine, such as at least one bacterium selected from bacteria of phylum Firmicutes, Bacteroidetes, Actinobacteria, Tenericutes, and Verrucomicrobia, and/or
- at least one polyphenol such as for example at least one polyphenol selected from quercetin, kaempferol, resveratrol, flavones (such as luteolin), flavan-3-ols or catechins, flavanones (such as naringinin), isoflavones, anthocyanidins, oligo-proanthocyanidins, and/or
- at least one mineral and/or at least one vitamin and/or at least one nutritional agent, and/or
- at least one pharmaceutical active ingredient preferentially selected from non-steroidal anti-inflammatory drugs, antibodies directed against pro-inflammatory targets (such as anti-TNFalpha or anti-IL6), anti-inflammatory targets, analgesics, antimicrobials, corticosteroids, anabolic steroids, antidiabetics, thyroid agents, antidiarrheals, cough suppressants, antiemetics, anti-ulcers, laxatives, anticoagulants, erythropoietin, immunoglobulins, immunosuppressors, growth hormones, hormonal medications, oestrogen receptor modulators, alkylating agents, antimetabolites, mitotic inhibitors, radiopharmaceuticals, antidepressants, antipsychotics, anxiolytics, hypnotics, sympathomimetics, stimulants, donepezil, tacrine, drugs for asthma, beta-agonists, inhaled steroids, leukotriene inhibitors, cromoglycates or cromoglycidic acids, epinephrine, domase alpha, cytokines, cytokine antagonists, Janus Kinase inhibitors, immunomodulators, lipid-lowering drugs, cholesterol-lowering drugs, antihypertension drugs.

According to a preferred object, the composition according to the invention is in any form acceptable to be administered to a subject, preferentially a human or non-human animal. Preferably, the composition according to the invention is in solid, liquid or lyophilized form.

When the composition is in liquid form, it may in particular comprise bacterial strains according to the invention and/or of the derived strain and/or a culture medium of said bacteria which makes it possible to maintain them, such as for example preferentially the anaerobic Columbia agar medium enriched with sheep blood, or an equivalent medium not containing any derived product of animal origin.

When the composition according to the invention is in solid form, the bacterial strains according to the invention and/or of the derived strain can be present in lyophilized form, and may also comprise excipients such as, for example, microcrystalline cellulose, lactose, sucrose, fructose, levulose, starches, stachyose, raffinose, amylum, calcium lactate, magnesium sulfate, sodium citrate, calcium stearate, polyvinylpyrrolidone, maltodextrin, galactooligosacchardes, fructooligosaccharides, pectins, beta-glucans, lactoglobulins, isomaltooligosaccharides, polydextroses, mannitol, sorbitol and/or glycerol.

According to another embodiment, the composition according to the invention is in a form suitable for oral, nasal, parenteral, rectal, sublingual, ocular, auricular, inhaled or cutaneous administration.

The composition may be in any suitable form. Thus, the composition according to the invention may be in a form selected from a powder, microencapsulated powder, capsule, tablet, pellet, granule, emulsion, suspension, suppository and syrup.

According to a particularly suitable embodiment, the composition according to the invention may be in gastro-resistant form, for example a coated tablet containing micro-encapsulated bacteria. Said composition can thus be provided with a gastro-resistant coating or a coating resistant to gastric juice, in order to ensure that the bacterium (bacteria) comprised in said composition can pass through the stomach. The release of the bacterium (bacteria) can thus occur for the first time in the upper intestinal tract.

The composition according to the invention may also be in the form of a food product, a beverage, a nutraceutical, a food additive, a food supplement or a dairy product.

When the composition according to the invention is comprised in a food supplement for oral administration, the latter can be present in capsules, gel capsules, soft capsules, tablets, sugar-coated tablets, pills, pastes, pellets, gums, drinkable solutions or emulsions, a syrup or a gel.

A food supplement according to the present invention may further comprise a sweetener, a stabiliser, an antioxidant, an additive, a flavouring agent and/or a colorant. The formulation of the latter is carried out by means of the usual methods for producing sugar-coated tablets, gel capsules, gels, hydrogels for controlled release, emulsions, tablets or capsules.

A composition according to the present invention may also be in the form of a nutritional composition. Such nutritional composition according to the present invention may be in the form of a yogurt, a cereal bar, breakfast cereals, a dessert, frozen food, a soup, a pet food, a liquid suspension, a powder, a tablet, a gum or a sweet.

A nutritional composition according to the present invention may further comprise at least one ingredient selected from: antioxidants, fish oils, DHA, EPA, vitamins, minerals, phytonutrients, protein, lipid, probiotics, prebiotics and combinations thereof.

According to another subject matter of the invention, the composition comprises $10^4$ to $10^{12}$ colony forming units (CFU) of bacteria per daily dose of composition to be administered, preferentially $10^6$ to $10^{12}$ colony forming units (CFU) of bacteria per daily dose of composition to be administered.

Preferentially, this corresponds to a daily dose of bacteria to be administered, regardless of the weight of the person or of the animal. Preferably, this dose is administered in a single time. More preferentially, the useful composition comprises $10^7$ to $10^{11}$ CFU of bacteria per daily dose to be administered, even more preferentially $10^9$ CFU. The bacteria are a mixture of bacteria corresponding or derived from the bacterial strain DSM 33407 and/or corresponding to the derived strain.

The term CFU (Colony Forming Unit) is a unit making it possible to count the number of bacteria capable of giving rise to a colony during propagation, that is to say viable bacteria. It should be understood that non-viable bacteria can also be present in the compositions and that in general they should not have a negative effect on the properties of the living bacteria of the composition, and, on the contrary, they can exert an effect on themselves.

Preferentially, the daily dose is measured per gram or millilitre of the final composition according to the invention.

According to another preferred object, when the composition according to the invention comprises a mixture of bacteria, said mixture comprising at least living bacteria, the composition preferentially comprises at least 1% of living bacteria (in number), more preferentially at least 10% of living bacteria (in number), even more preferentially at least 50% (in number).

The living bacteria are a mixture of bacteria corresponding to the bacterial strain DSM 33407 and/or corresponding to the strain derived from said strains.

In the case of the implementation of a supernatant of any one of the aforementioned bacterial strains, the composition according to the invention including said supernatant may in particular comprise a content thereof of between 0.1 and 99% by weight, namely from 5 to 95% by weight, in particular from 10 to 90% by weight and more particularly from 15 to 85% by weight, relative to the total weight of the composition.

Thus, a composition according to the invention may comprise a supernatant content of between 0.1 and 99% by weight, namely from 5 to 95%, in particular from 10 to 90% by weight, more particularly from 15 to 85% by weight, relative to the total weight of the composition.

According to a particular embodiment, the composition according to the invention also comprises at least one pharmaceutically acceptable excipient.

When the composition comprises such a pharmaceutically acceptable excipient, the composition according to the invention is advantageously a pharmaceutical composition.

Thus, according to another subject matter, the invention also relates to a pharmaceutical composition comprising the ingredient(s) included in the composition according to the invention and according to one of any embodiments described above.

Said pharmaceutical composition according to the invention has at least one application in the improvement of the physical, physiological or psychological well-being of a subject with a disease, which results in an improvement in the general state of health of said subject or a reduction in the risk of disease. Said pharmaceutical composition may be a medicament.

Therapeutic and Non-Therapeutic Use

Thus, another aspect of the invention relates to the bacterial strain according to the invention and/or the derived strain, the supernatant according to the invention, or the composition according to the invention, or the pharmaceutical composition according to the invention for its use as a medicament.

In particular, the invention makes it possible to provide an effective amount of bacterial strains according to the invention or of the derived strain, to be used as a medicament.

Such use as a medicament necessarily has a preventive and/or therapeutic effect, that is to say that of reducing the risk of getting a disease and/or decreasing or stabilising or reversing or interrupting the progression of the disease.

The use as a medicament in the context of the present invention refers to human or veterinary use, said medicament is then administered to a human subject or a non-human animal subject.

Human subject is also understood to mean an adult or child or a baby, including a newborn or an infant.

Preferentially, the invention relates to the bacterial strain according to the invention and/or the derived strain, or the bacteria derived from said strains according to the invention, the supernatant according to the invention, or the composition according to the invention, or the pharmaceutical composition according to the invention for its use as a medicament, in particular in the prevention and/or treatment of dysbiosis of the microbiota, in particular intestinal microbiota and/or diseases associated with dysbiosis of the intestinal microbiota and/or chronic diseases and/or obesity and/or metabolic diseases and/or inflammatory diseases and/or cancers.

According to one embodiment, the invention also relates to the bacterial strain according to the invention and/or the derived strain, the supernatant according to the invention, or the composition according to the invention, or the pharmaceutical composition according to the invention for its use as a medicament, in the prevention and/or treatment of chronic diseases associated with dysbiosis of the microbiota and/or metabolic diseases, preferentially metabolic diseases associated with dysbiosis of the microbiota and/or obesity and/or inflammatory diseases, preferentially inflammatory diseases associated with dysbiosis of the microbiota and/or cancers, preferentially cancers linked to metabolism.

Preferably, the invention relates to the bacterial strain according to the invention and/or the derived strain, the supernatant according to the invention, or the composition according to the invention, or the pharmaceutical composition according to the invention for its use as a medicament, in the prevention and/or treatment of at least one disease selected from:

- metabolic diseases, selected from non-insulin-dependent diabetes, gestational diabetes, NASH, hepatic steatosis, pancreatic steatosis, hyperlidemia, hypercholesterolemia, infertility linked to excess weight, urinary incontinence linked to excess weight,
- other chronic metabolic diseases, including thyroiditis,
- cardiac and vascular diseases, selected from atherosclerosis, thrombopathies, acute pericarditis and chronic constrictive pericarditis, arterial hypertension, vasculartis
- liver and bile duct diseases, selected from hepatitis, primary biliary cirrhosis, primary sclerosing cholangitis, cirrhosis, hepatic encephalopathy, vesicular lithiasis
- joint diseases linked to excess weight, selected from osteopenia, osteoporosis, osteoarthritis, vertebral disc inflammation
- neurodegenerative diseases, selected from Alzheimer's disease, Parkinson's disease, motor neuron diseases such as amyotrophic lateral sclerosis, primitive lateral sclerosis and Kennedy disease
- cancers linked to metabolism and/or to dysbiosis of the microbiota, selected from hepatocarcinomas, gastrointestinal tract cancers such as oesophageal, stomach and colorectal cancer, pancreatic carcinoma, neuroendocrine tumours (NETs) of the gastrointestinal-pancreatic system, hepatic tumours, gallbladder and bile duct tumours, renal tumours, glioblastoma, lymphoma, multiple myeloma, chronic myeloid leukaemia, chronic myeloproliferative diseases, lung carcinoma
- auto-immune diseases, selected from insulin-dependent diabetes, rheumatoid arthritis, ankylosing spondylitis, psoriatic arthritis, systemic lupus erythematosus, polyendocrine autoimmune syndrome
- atopic skin diseases, selected from eczema, psoriasis
- chronic inflammatory bowel diseases, selected from Crohn's disease, hemorrhagic ulcerative rectocolitis, diverticulitis, oesophagitis, gastritis, pancreatitis, gastrointestinal ulcers, irritable bowel syndrome
- respiratory function disorders, selected from asthma, cystic fibrosis, chronic obstructive pulmonary disease, interstitial lung diseases and pulmonary fibroses, sleep apnoea syndrome (OSAS)
- pneumonias, selected from infectious pneumonia, influenza pneumonia and avian flu, severe acute respiratory syndrome (SARS), *pneumocystis* pneumonia
- infectious diarrhoea, selected from *Clostridium difficile* infection, EHEC infection, *salmonella* gastroenteritis, *campylobacter* enteritis, food poisoning by enterotoxin-producing bacteria, cholera, yersinosis, shigellosis, cryptosporidiosis, literiosis
- food allergies, selected from celiac disease, lactose intolerance, bile salt malabsorption syndrome
- inflammatory kidney disorders or others related to dysbiosis of the microbiota, selected from urethritis, chronic renal failure, urolithiasis
- other inflammatory disorders, selected from multiple sclerosis, lymphangitis
- neurological diseases related to dysbiosis of the microbiota, selected from anorexia, bulimia, depression, bipolar syndrome, autism, schizophrenia, Tourette syndrome.

According to a particularly advantageous embodiment, the invention relates to the prevention and/or treatment of at least two diseases selected from the preceding list, preferentially at least three, more preferentially at least four and even more preferentially at least five.

According to a final subject matter, the invention also relates to a non-therapeutic use of a bacterial strain according to the invention, and/or of a supernatant according to the invention, and/or composition according to the invention for maintaining and/or reinforcing the intestinal microbiota and/or supporting the diversity of the intestinal microbiota and/or promoting the increase of beneficial bacteria in the intestinal microbiota and/or promoting the loss of weight in a healthy subject, preferentially a human subject or non-human animal.

For the purposes of the invention, the term "healthy subject" is intended to mean a non-ill subject not suffering from disease, in particular not suffering from a disease selected from:

- metabolic diseases, selected from non-insulin-dependent diabetes, gestational diabetes, NASH, hepatic steatosis, pancreatic steatosis, hyperlidemia, hypercholesterolemia, infertility linked to excess weight, urinary incontinence linked to excess weight,
- other chronic metabolic diseases, including thyroiditis,
- cardiac and vascular diseases, selected from atherosclerosis, thrombopathies, acute pericarditis and chronic constrictive pericarditis, arterial hypertension, vasculartis
- liver and bile duct diseases, selected from hepatitis, primary biliary cirrhosis, primary sclerosing cholangitis, cirrhosis, hepatic encephalopathy, vesicular lithiasis joint diseases linked to excess weight, selected from osteopenia, osteoporosis, osteoarthritis, vertebral disc inflammation neurodegenerative diseases, selected from Alzheimer's disease, Parkinson's disease, motor neuron diseases such as amyotrophic lateral sclerosis, primitive lateral sclerosis and Kennedy disease cancers linked to metabolism and/or to dysbiosis of the microbiota, selected from hepatocarcinomas, gastrointestinal tract cancers such as oesophageal, stomach and colorectal cancer, pancreatic carcinoma, neuroendocrine tumours (NETs) of the gastrointestinal-pancreatic system, hepatic tumours, gallbladder and bile duct tumours, renal tumours, glioblastoma, lymphoma, multiple myeloma, chronic myeloid leukaemia, chronic myeloproliferative diseases, lung carcinoma auto-immune diseases, selected from insulin-dependent diabetes, rheumatoid arthritis, ankylosing spondylitis, psoriatic arthritis, systemic lupus erythematosus, polyendocrine autoimmune syndrome atopic skin diseases, selected from eczema, psoriasis chronic inflammatory bowel diseases, selected from Crohn's disease, hemorrhagic ulcerative rectocolitis, diverticulitis, oesophagitis, gastritis, pancreatitis, gastrointestinal ulcers, irritable bowel syndrome respiratory function disorders, selected from asthma, cystic fibrosis, chronic obstructive pulmonary disease, interstitial lung diseases and pulmonary fibroses, sleep apnoea syndrome (OSAS)

pneumonias, selected from infectious pneumonia, influenza pneumonia and avian flu, severe acute respiratory syndrome (SARS), *pneumocystis* pneumonia infectious diarrhoea, selected from *Clostridium difficile* infection, EHEC infection, *salmonella* gastroenteritis, *campylobacter* enteritis, food poisoning by enterotoxin-producing bacteria, cholera, yersinosis, shigellosis, cryptosporidiosis, listeriosis food allergies, selected from celiac disease, lactose intolerance, bile salt malabsorption syndrome inflammatory kidney disorders or others related to dysbiosis of the microbiota, selected from urethritis, chronic renal failure, urolithiasis other inflammatory disorders, selected from multiple sclerosis, lymphangitis neurological diseases related to dysbiosis of the microbiota, selected from anorexia, bulimia, depression, bipolar syndrome, autism, schizophrenia, Tourette syndrome.

The invention is now illustrated by examples of bacteria useful according to the invention, methods of cultures of these bacteria, examples of compositions containing them and results of tests demonstrating the efficacy of the invention, which are presented by way of illustration only.

EXAMPLES

Example 1: Characterisation of *C. minuta* According to the Invention Deposited Under the Number DSM 33407

The bacterial strain *C. minuta* DSM 33407 can be characterised by the following method.

The native bacteria of the DSM 33407 strain (10 μL of culture medium assayed at $10^9$ CFU/mL) were deposited on grids made of ionised carbon (Delta Microscopy, Toulouse, France) and a negative colouring was carried out with Nano-Tungsten (Nano-W, Nanoprobes, LFG Distribution, France).

The observation of the bacteria mounted on the grid was carried out with a transmission electron microscope (Talos F200S G2—Thermofisher—Eindhoven) at 200 kV, equipped with a 4K*4K One View camera (Gatan, Paris, France). The preparation of the samples, thus the acquisitions, were carried out at the Bordeaux Imaging Center (member of France-BioImaging, ANR-10-INBS-04). Gram staining was carried out following the classic procedure. The bacterium according to the invention has the following characteristics: gram negative, strict anaerobic, without formation of spores and resistant to bile acids. From the DSM 33407 strain, the generation time (G) is between 3 h and 12 h and the growth rate (K) is 0.11 G/hour.

FIG. 1 shows the image of a bacterium *Christensenella minuta* according to the invention produced by transmission electron microscopy in negative colouring (magnification: 36k×). The average dimensions of a bacterium of the DSM 33407 strain are: length=1.77+−0.34 mm; width=1.52+−0.03 mm; with a membrane thickness=35 nm (mean obtained from 40 bacteria).

Example 2: Comparison Between the Strain According to the Invention (DSM 33407) and Strains of *C. minuta* from the Prior Art The inventors also compared the strain according to the invention (DSM 33407) with other strains of *C. minuta* such as the reference strain deposited under number DSM 22607, the strain deposited under number DSM 32891 and the strain deposited under number DSM 33715 according to several parameters such as the sequence of the 16S rDNA, the size of the base pair genome (bp), the full genome phylogenetic distance (ANI), the coding sequence number (CDS) and examples of genes specific to the strain.

The results are presented in tables 1 to 3 below.

TABLE 1

| | 16S rDNA | Size of genome (bp) | ANI (genome homology %) | CDS (Coding Sequence number) | Example of specific genes |
|---|---|---|---|---|---|
| DSM22607 | SEQ ID NO: 1 | 2944440 | 99.82% | 2765 | Coding gene for the lexA repressor |
| DSM 33407 | SEQ ID NO: 1 | 2791808 | | 2595 | Coding gene for the phosphoglucosamine mutase glmM_1 |

TABLE 2

| | 16S rDNA | Size of genome (bp) | ANI (genome homology %) | CDS (Coding Sequence number) | Example of specific genes |
|---|---|---|---|---|---|
| DSM 32891 | SEQ ID NO: 1 | 2841506 | 99.61% | 2663 | Coding gene for thioredoxin-disulfide reductase trxB |
| DSM 33407 | SEQ ID NO: 1 | 2791808 | | 2595 | Coding gene for glycerol dehydrogenase gldA |

TABLE 3

| | 16S rDNA | Size of genome (bp) | ANI (genome homology %) | CDS (Coding Sequence number) | Example of specific genes |
|---|---|---|---|---|---|
| DSM 33407 | SEQ ID NO: 1 | 2791808 | 99.69% | 2595 | Coding gene for PknD (serine/threonine protein kinase) |
| DSM 33715 | SEQ ID NO: 1 | 2959549 | | 2773 | Coding gene for TrxB (thioredoxin-disulfide reductase) |

Thus, the strain according to the invention (DSM 33407) has the same 16S rDNA sequence as the other three strains of *C. minuta* despite having different metabolic properties and anti-inflammatory potential. However, the size of the genome, the whole genome, the coding sequence number and certain genes specific to said strain make it possible to differentiate it from other strains of *C. minuta.*

Example 3: Anti-Inflammatory Effect of the Strain According to the Invention

In the present study, the inventors studied the immunomodulatory and anti-inflammatory effect of the DSM 33407 strain.

The study protocol is as follows. The HT-29 cells (ECACC) were inoculated into 24-well plates at $3\times10^5$ cells per well in McCoy's 5A (Gibco) medium supplemented with 10% foetal calf serum (FCS, Gibco) and incubated at 37° C./5% CO2-for-24 h. The cells were washed with PBS-1× (Gibco) and cultivated for an additional 24 h in McCoy's 5A medium at 2% FCS. The cells were then stimulated for 6 hours with 5 ng/ml of TNF-α in the presence of 10% of supernatant in stationary phase of DSM 33407 or of bacterial culture medium as control (ctrd). After 6 h, the cell culture supernatants were collected and stored at −80° C. until the IL-8 was quantified by ELISA. The IL-8 assay was carried out by BioLegend specific ELISA, according to the manufacturers instructions. The absorbance at 460 nm was read using the FluoStar Omega microplate reader of BMG Labtech.

To evaluate the immunomodulatory effect of the DSM 33407 strain, the HT-29 cells were stimulated with the pro-inflammatory cytokine TNF-α and the supernatant of DSM 33407 in stationary phase for 6 h. Chemokine IL-8 is secreted by HT-29 in an inflammatory state induced by TNF-α (Ctrl). The values represent the average normalised as a percentage relative to the control+TNF-α, representing the secretion of IL-8 induced by stimulation with TNF-α, i.e. 100%.

Figure 2:
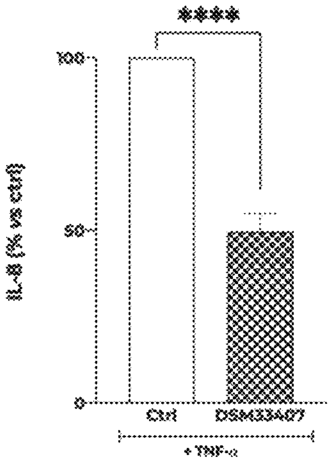
FIG. 2 shows the immuno-modulating effect of the supernatant of DSM 33 407 on the IL-8-producing HT-29 colon adenocarcinoma line after stimulation with TNF-α. Six independent experiments were carried out, in duplicate.

FIG. 2 shows that, in the presence of the supernatant of the DSM 33407 strain, the IL-8 secretion is reduced by 50% relative to the control ($p<0.0001$, Dunnett's multiple comparisons test). The supernatant of the DSM 33407 strain therefore has an immunomodulatory and anti-inflammatory effect.

Example 4: Anti-Inflammatory Effect of the Strain According to the Invention

In the present study, the inventors studied the anti-inflammatory effect of the DSM 33407 strain over a total of 30 male mice.

The study protocol is as follows. A total of thirty (30) male C57Bl6 mice aged 7 weeks were exposed either to a standard diet (ND for normal diet), or to a high fat diet (HFD45: 45% of the calorie intake comes from fats) for 12 consecutive weeks. During this time, the animals were treated daily by oral feeding, either with DSM 33407 (treated group), or with its vehicle (control group). During the study, the weight and the food intake were monitored. Each group was composed of 10 mice. Blood levels of an adipokine considered as an indirect inflammatory marker, resistin, were measured. The quantification was carried out using custom built BIORAD plates (Biorad, Mames la Coquette, France). All the samples were evaluated in duplicate.

The results were analysed by one-way ANOVA with multiple comparisons (Benjamini, Krieger and Yegutieli test) using the Prism8 software (Graphpad). All the results are expressed as a mean±standard deviation (MSD) and the significance threshold is set at $p<0.05$ for all analyses.

Figure 3:
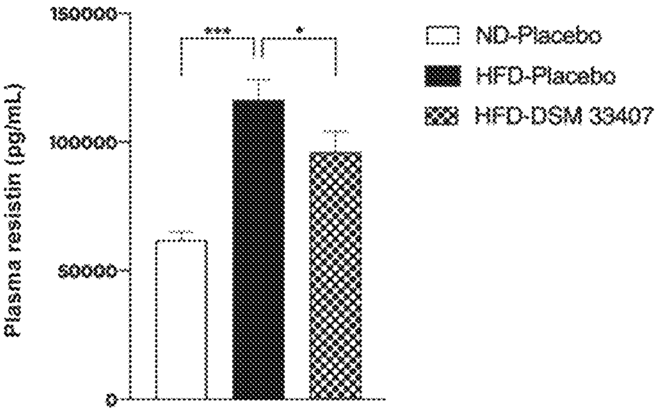
FIG. 3 shows the fasting plasma resistin levels measured after 12 weeks of exposure, either with a standard diet, or with a high fat diet with or without treatment with DSM 33407. Resistin is a cytokine also produced by the adipose tissue in mice, and it accelerates the differentiation of pre-adipocytes into adipocytes.

FIG. 3 shows that the fasting plasma resistin levels measured after 12 weeks of HFD45 exposure were significantly reduced in the group of animals treated with DSM 33407. Thus, in combination with a limitation of the weight gain, the daily administration of DSM 33407 made it possible to significantly reduce the circulating levels (fasting blood) of resistin.

Example 5: Anti-Inflammatory Effect of the Strain According to the Invention

In the present study, the inventors studied the anti-inflammatory effect of the DSM 33407 strain over a total of 30 male mice according to the protocol described in example 3, with the difference that the diet lasted 6 consecutive weeks. At the end of the study, the animals were sacrificed and the tissues of interest, here the livers, were immediately removed and frozen while awaiting their analysis. The frozen tissues were transformed in nitrogen powder. The ground materials were then lysed and homogenised cold.

After quantification (Bradford), the extracted proteins were diluted and the samples normalised at 1 mg/mL (lysis buffer with 1% Bovine serum Albumin). The assay of the proteins of interest (IL-6 for Interteukin-6, RANTES for regulated on activation, normal T cell expressed and secreted, TNFα for tumour necrosis factor alpha) were made according to the manufacturer's recommendations of the quantification kit (BioLegend). The quantification data were analysed by (i) evaluating their distribution (Shapiro-Wilk test), then via (ii) one-way ANOVA with multiple comparison (Dunett) via the Prism9 software (GraphPad). The data are expressed as a mean t standard deviation (MSD) and the significance threshold is set at $p<0.05$ for all analyses. (Statistic symbols on graphs: *$p<0.05$, $p<0.01$, *$p<0.001$, ****$p<0.0001$).

Figure 17:
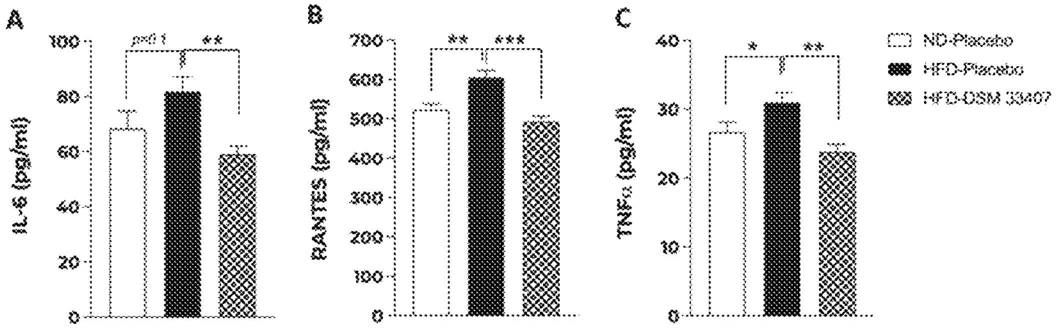
FIG. 17 shows the anti-inflammatory effect of the DSM 33407 strain in mice subjected to a fatty diet for 6 weeks on levels of cytokines IL-6 (A), RANTES (B), and TNFα (C).

The results are presented in FIG. 17. Exposure to a fatty diet for 6 weeks induced a significant increase in IL-6 cytokine levels; RANTES, and TNFα in the mice having received the placebo. This increase in hepatic cytokines was not observed in animals under a fatty diet treated with DSM 33407. Indeed, the concentrations of these 3 proteins are significantly lower than in the placebo group, and similar to animals under a standard diet.

Example 6: Anti-Inflammatory Effect of the Strain According to the Invention on a Model In Vitro The study aims to evaluate the anti-inflammatory effect of DSM33407 in a model in vitro based on human immune cells by measuring the amount of chemokine (resistin) produced by human peripheral blood mononuclear cells (PBMCs) after stimulation to LPS in the presence or absence of DSM 33407 (bacterium or supernatant).

The study protocol is as follows. The PBMCs isolated from blood from healthy and cryo-preserved donors (Lonza Biosciences) were thawed and then passed into RPMI-1640 Glutamax medium (Gibco) containing 10% FBS (Gibco) in a humidified atmosphere at 5% CO2-for-24 hours before the start of the study. The PBMCs were seeded at 1 million per 24-well plate. The stimulation was carried out with lipopolysaccharide (LPS O111B4 *E. coli* at 100 ng/ml). 50 μL of culture medium (control), of culture supernatant of DSM 33407, or of DSM 33407 bacteria (MOI=50 bacteria/eukaryotic cell) were added as a function of the tested condition. The co-cultures were maintained for 24 hours. Next, the final supernatants were collected and the resistin was quantified by ELISA (R&D systems), following the manufacturer's guidelines. Absorbance was read at 450 nm (FLUOStar Omega; BMG Labtech). The resistin quantification data present in the medium were analysed by (i) evaluating their distribution (Shapiro-Wilk test) then via (ii) one-way ANOVA with multiple comparison (Dunett) via the Prism9 software (GraphPad). The data are expressed as a mean±standard deviation (MSD) and the significance threshold is set at $p<0.05$ for all analyses. (Statistic symbols on graphs: *$p<0.05$, $p<0.01$, *$p<0.001$, ****$p<0.0001$)

Figure 18:
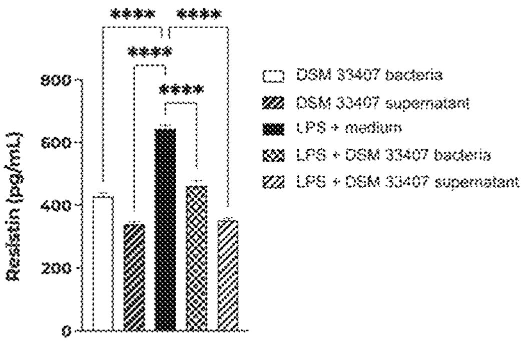
FIG. 18 shows the anti-inflammatory effect of DSM33407 in vitro on human immune cells by measuring the amount of cytokine (resistin) produced by human peripheral blood mononuclear cells (PBMCs).

The results are shown in FIG. 18. The administration of the DSM 33407 bacterium alone or of its supernatant made it possible to induce a secretion of resistin by the PBMCs. The application of LPS, a powerful pro-inflammatory, induced a strong increase in the resistin. This increase was significantly stronger than that induced in the presence of DSM 3407. The presence of DSM 33407 (bacterium or supernatant) made it possible to greatly limit the increase in resistin normally induced by an application of LPS.

Example 7: Effect of the Strain According to the Invention on the Integrity of the Intestinal Barrier In the present study, the inventors studied the protective effect on the intestinal epithelium of the DSM 33407 strain.

The study protocol is as follows. The Caco-2 (ECACC) cells were seeded at $2\times10^4$ cells per well in 24-well plates containing inserts with a permeable membrane made of Transwell polyester (Corning Life Science). The cells were cultivated in DMEM medium supplemented with 20% foetal calf serum (FCS, Gibco) and incubated at 37° C./5% CO2. The transepithelial electrical resistance (TEER) was verified every day from the seventh day of culture using an EVOM3 ohmmeter (WPI). The medium was replaced every 2 days for 8 to 10 days, until the optimal TER was reached (2000 $\Omega\cdot cm^2$). When the reference TEER was reached, the cells were treated in the apical compartment with DSM 33407 at a MOI of 50 or PBS 1×/Glycerol 10% (control) for 3 h, then 100 ng/ml of TNF-α was added or not in the basal compartment. The TEER was measured just before the addition of TNF-α (TO) and 6 h (T6H) after the addition of TNF-α.

To evaluate the capacity of the DSM 33407 strain to restore or reinforce the intestinal barrier, the Caco-2 cells in polarised monolayer were pre-treated with DSM 33407, then sensitised with TNF-α. The TEER was compared to T0 (before addition of TNF) and T6H. The values represent the mean normalised relative to the control—TNF-α, representing the basal TEER.

Figure 4:
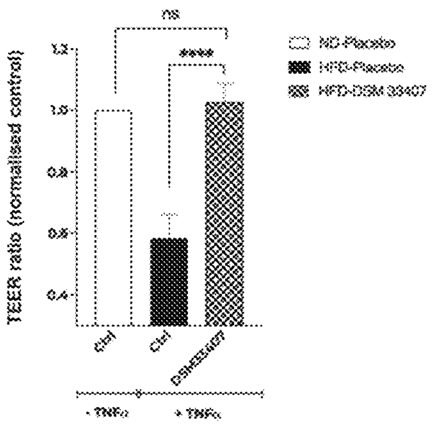
FIG. 4 shows the effect of the DSM 33407 strain on the integrity of the intestinal barrier measured by the TEER method (Transepithelial Electrical Resistance) on Caco2 cells (human colon carcinoma). The TEER method is based on the measurement of the transmembrane electrical resistance as the indicator of cohesion of tight junctions. The membrane is destabilized by the addition of a pro-inflammatory agent (TNF-α) in the presence or absence of DSM 33407 bacteria. The control (Ctrl)+/−TNF-α corresponds to PBS 1×/Glycerol 10%, a re-suspension medium for the bacterial strain DSM 33407.

The results in FIG. 4 indicate that the treatment of Caco-2 with TNF-α induces an increase in permeability (Ctrl+TNF-α). The DSM 33407 strain is thus capable of restoring the epithelial barrier, with a return to the basal level (Ctrl−TNF-α).

Example 8: Protective Effect of the Strain According to the Invention on the Intestinal Barrier The inventors have studied the protective effect of DSM33407 on the intestinal barrier during a protocol for inducing obesity by a fatty diet by studying the expression level (m RNA) of tight junction proteins of the colon.

The study protocol is as follows. Thirty (30) male C57Bl6 mice aged 7 weeks were exposed either to a standard diet (ND for normal diet), or to a high fat diet (HFD: 45% of the calorie intake comes from fats) for 4 consecutive weeks. During this period, the animals were treated daily by oral feeding, either with DSM 33407 (treated group), or with a vehicle (placebo; control group). At the end of the study, the animals were sacrificed and the tissues of interest, here the colons, were immediately removed and frozen while awaiting their analysis.

The messenger RNA extraction was carried out by means of Rneasy Plus (Qiagen) kits, the complementary DNAs generated by the negative transcription (iScript Advanced cDNA synthesis, Bio-Rad) and the amplification carried out by real-time quantitative PCR (SsoAdvanced SYBR Green Universal Supermix (Bio-Rad). Specific primers of the genes of interest (Zo1 for zonula occludens 1, Ocln for Occludin1, Cldn 1 for Claudine1) had been developed and validated beforehand (Bio-Rad). The study was carried out in triplicate. The PCR cycle data were analysed by (i)

evaluating their distribution (Shapiro-Wilk test), then via (ii) one-way ANOVA with multiple comparison (Dunett) via the Prism9 software (GraphPad). The data are expressed as a mean±standard deviation (MSD) and the significance threshold is set at $p<0.05$ for all analyses. (Statistic symbols on graphs: *p<0.05, p<0.01, p<0.001, ****p<0.0001).

Figure 19:
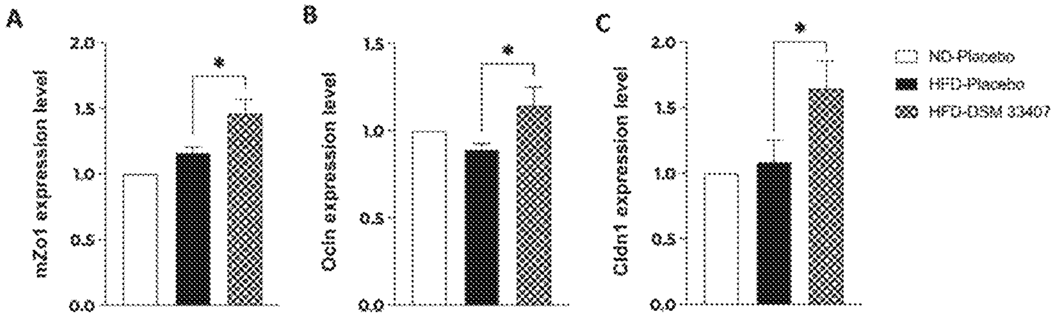
FIG. 19 shows the protective effect of the DSM 33407 strain on the intestinal barrier by measuring the expression level of tight junction proteins mZo1 (A), Ocln (B) and Cldn1 (C) in the colon.

The results in FIG. 19 make it possible to observe a significant increase in expression levels for the proteins Zo1, Ocln and Cldn 1 after 6 weeks of treatment in animals under a fatty diet and treated with DSM 33407 in comparison with the animals receiving the placebo. This study thus makes it possible to confirm the protective role of the strain according to the invention on the intestinal barrier of a subject suffering from obesity since these proteins are responsible for maintaining the seal of the barrier.

Example 9: Effect on the Weight Gain and the Feed Efficiency of the Strain According to the Invention In the present study, the inventors studied the effect of the DSM 33407 strain on the weight gain.

The study protocol is as follows. A total of thirty (30) male C57Bl6 mice aged 7 weeks were exposed either to a normal diet (ND for normal diet; 10 mice) or to a high fat diet (HFD45, 45% of the calorie intake comes from fats) for 4 consecutive weeks (20 mice). During this time, the animals were treated daily by oral feeding, either with DSM 33407 (treated group), or with its vehicle (control group). Each group was composed of 10 mice. During the study, the weight and the food intake were monitored, thus making it possible to estimate the feed efficiency (FE; in g/kcal). In order to compare the impact of treatments on the FE, the area under the curve (AUC) was measured between D0 and D27. The results were analysed by two-way ANOVA with multiple comparisons (Benjamini, Krieger and Yegutieli test or Dunett test) via the Prism8 software (Graphpad). All the results are expressed as a mean±standard deviation (MSD) and the significance threshold is set at $p<0.05$ for all analyses. (Statistic symbols on graphs: *p<0.05, p<0.01, *p<0.001).

Figure 5:
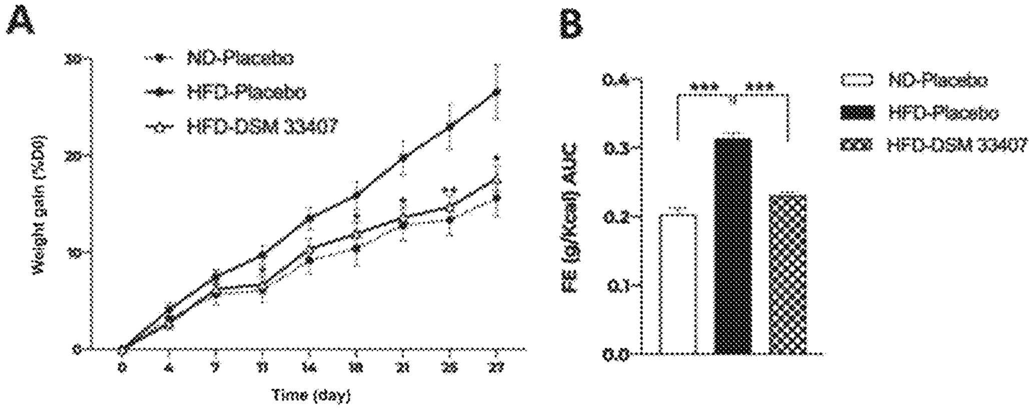
FIG. 5A shows the efficiency on the weight loss. During exposure to an obesogenic diet of HFD45 type (a rich diet providing 45% of the calories in the form of fat), the daily treatment with DSM 33407 protects against weight gain.
FIG. 5B shows the feed efficiency. During exposure to an obesogenic diet of HFD45 type (a rich diet providing 45% of the calories in the form of fat), the daily treatment with DSM 33407 limits the feed efficiency (i.e. the gain in weight per gram of ingested food).

The animals under HFD45 all gained significantly more weight than the animals that remained under ND. The treatment with DSM 33407 significantly prevented the weight gain induced by exposure to the HFD45 obesogenic diet (FIG. 5). The first significant effects on the weight gain appear as soon as the 11*th* day of treatment. In the group treated with DMS 33407, the feed efficiency was significantly reduced compared to the group of animals under placebo.

Example 10: Effect on the Weight Gain and the Feed Efficiency of the Strain According to the Invention at Different Doses In the present study, the inventors studied the effect of the DSM 33407 strain at different doses on the weight gain.

The study protocol is as follows. A total of thirty (30) male C57Bl6 mice aged 7 weeks were exposed either to a standard diet (ND for normal diet; mice), or to a high fat diet (HFD45, 45% of the calorie intake comes from fats, mice) for 6 consecutive weeks. During this time, the animals were treated daily by oral feeding, either with 4 different doses of DSM 33407 (treated group) or with its vehicle (placebo control group). The doses tested were 1.5 $10^7$ CFU/mL, 1.5 $10^8$ CFU/mL, 1.5 $10^9$ CFU/mL (reference dose), and 1.5 $10^{10}$ CFU/mL. Each group was composed of 10 mice. During the study, the weight and the food intake were monitored, thus making it possible to estimate the feed efficiency (FE; in g/kcal). In order to compare the impact of treatments on the FE, the area under the curve (AUC) was measured between DO and D40.

The results were analysed by two-way ANOVA with multiple comparisons (Benjamini, Krieger and Yegutieli test or Dunett test) via the Prism8 software (Graphpad). All the results are expressed as a mean±standard deviation (MSD) and the significance threshold is set at $p<0.05$ for all analyses. (Statistic symbols on graphs: *p<0.05, p<0.01, p<0.001).

Figure 6:
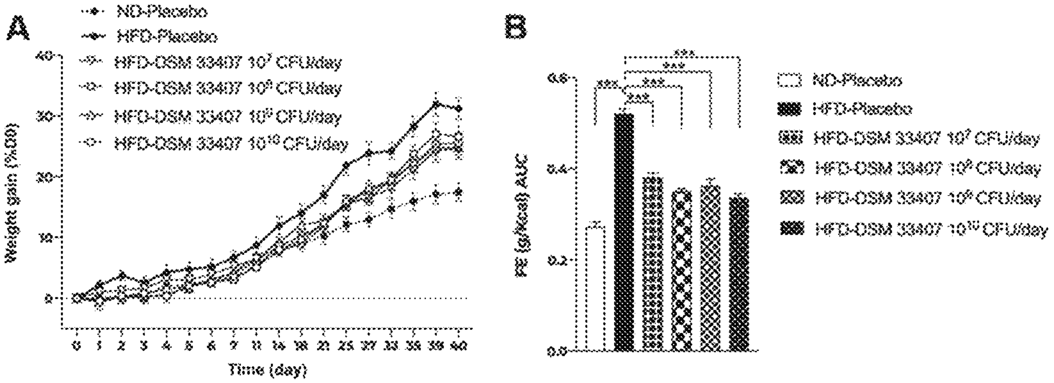
FIG. 6A shows the efficiency on the loss of weight at different doses. During exposure to an obesogenic diet of HFD45 type (45% of the calories provided by fat), all the doses of DSM 33407 tested between $1 \cdot 10^7$ and $1 \cdot 10^{10}$ CFU/mL protected the animals against weight gain.
FIG. 6B shows the feed efficiency (FE) at different doses. During exposure to an obesogenic diet of HFD45 type (45% of the calories provided by fat), all the doses of DSM 33407 tested between $1 \cdot 10^7$ and $1 \cdot 10^{10}$ CFU/mL limited the feed efficiency.

The animals under HFD45 all gained significantly more weight than the animals that remained under ND. All the doses of DSM 33407 tested between $1\cdot10^7$ and $1\cdot10^{10}$ CFU/mL significantly prevented the weight gain induced by exposure to the HFD45 obesogenic diet (FIG. 6). The first significant effects on the weight gain appear as soon as the 18th day of treatment. The four concentrations exhibited similar effects. In all groups treated with DSM 33407, the feed efficiency was significantly reduced compared to the group of animals under placebo.

Example 11: Effect on the Weight Gain and the Persistence of the Effect, Including after the Treatment has been Stopped In the present study, the inventors studied the effect of the DSM 33407 strain on the weight gain and the persistence of this effect after stopping the treatment.

The study protocol is as follows. A total of forty (40) male C57Bl6 mice aged 7 weeks were exposed either to a standard diet (ND for normal diet; 10 mice), or to a high fat diet (HFD45, 45% of the calorie intake comes from fats, 30 mice) for 7 consecutive weeks. During this time, the animals were treated daily by oral feeding with DSM 33407 (treated group: $1\cdot10^9$ CFU/mL), with its vehicle (placebo control group), or with Orlistat (standard obesity treatment). All of the treatments were stopped and the animals remained under HFD45 for 3 additional weeks. Each group was composed of 10 mice. The objective here was to test the potential persistence of the effect of DSM 33407 on the weight gain. To compare the impact of the treatments on the weight gain, the area under the curve was measured between DO and D48 (treatment period) and between D48 and D67 (washing period).

The daily weight tracking results were analysed by two-way ANOVA with multiple comparisons (Benjamini, Krieger and Yegutieli test), and the results of area under the curve were analysed by one-way ANOVA with multiple comparisons (Tukey test). All the results are expressed as a mean±standard deviation (MSD) and the significance threshold is set at $p<0.05$ (statistical symbols in the graphs: *p<0.05, ***p<0.001).

Figure 7:
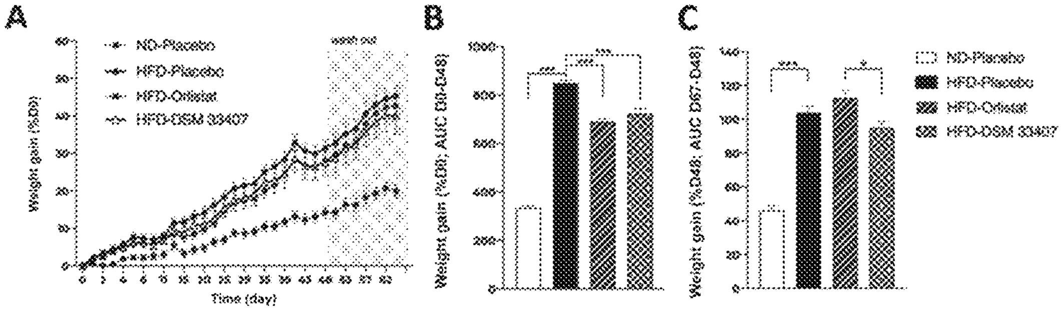
FIG. 7A shows the persistence of the effect of the DSM 33407 treatment after stopping of the treatment. During exposure to an obesogenic diet of HFD45 type, a daily treatment with Orlistat (used here as control) or DSM 33407 protects against weight gain.
FIG. 7B shows the persistence of the effect of the DSM 33407 treatment after stopping of the treatment. During exposure to an obesogenic diet of HFD45 type, a daily treatment with Orlistat (used here as control) or DSM 33407 protects against weight gain.
FIG. 7C shows the persistence of the effect of the DSM 33407 treatment after stopping of the treatment. Upon stopping the treatments, the animals under Orlistat rapidly gained weight, contrary to the animals treated with DSM 33407. ND: Normal maintenance diet for animals.

Here again, the animals under HFD45 all gained significantly more weight than the animals that remained under ND. The treatment with DSM 33407 significantly prevented the weight gain induced by exposure to the HFD45 obesogenic diet as represented in FIG. 7. The observed effect is comparable to that observed in animals treated with standard obesity treatment (Orlistat). During the 3 weeks following the stopping of the treatments, the animals which were under Orlistat had an acceleration of their weight gain, rapidly bringing them closer to the group of animals which were under placebo. Conversely, the animals under DSM 33407 maintained the protection against the weight gain. These results indicate a persistence of beneficial effects of DSM 33407 during the 3 weeks following the stopping of the treatment, during exposure to an obesogenic diet.

Example 12: Effect of the Strain According to the Invention on the Loss of Weight During a Change in Diet In the present study, the inventors studied the effect of the DSM 33407 strain on the loss of weight during a change in diet in order to evaluate the impact of a treatment with DSM 33407 on the weight of obese animals during a change in diet.

The study protocol is as follows. A total of thirty (30) obese male C57Bl6 mice aged 18 weeks raised under a high fat diet (HFD60, 60% of the calorie intake comes from fats) were fed with the vehicle of DSM 33407 for one week. At DO, certain animals were placed under a standard diet (ND for normal diet; 10 mice) for 4 weeks. The other animals were placed under a lower fat diet (HFD45, 45% of the calorie intake comes from fats; 20 mice) for 4 weeks. These animals were treated with DSM 33407 ($1.5 \cdot 10^9$ CFU/mL; 10 mice) or with its vehicle (placebo control group). During the study, the weight and the food intake were monitored, thus making it possible to estimate the feed efficiency (FE; in g/kcal). The main objective of the study was to evaluate the impact of a treatment with DSM 33407 on the weight of the animals during a change in diet. In order to compare the impact of treatments on the weight and the FE, the area under the curve (AUC) was measured between DO and D28.

The daily weight tracking results were analysed by two-way ANOVA with multiple comparisons (Benjamini, Krieger and Yegutieli test), and the results of area under the curve were analysed by one-way ANOVA with multiple comparisons (Tukey test). All the results are expressed as a mean±standard deviation (MSD) and the significance threshold is set at $p<0.05$ (statistical symbols in the graphs: **$p<0.001$).

Figure 8:
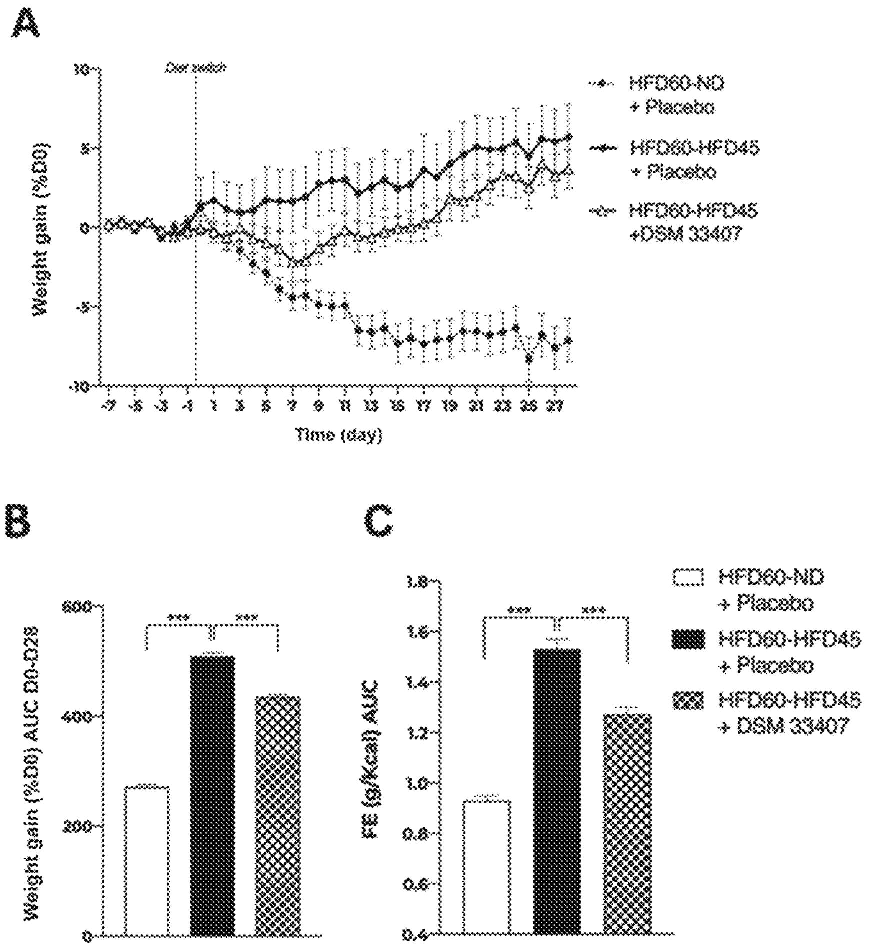
FIG. 8A shows the efficiency on the loss of weight after a change to a diet less rich in fat in obese mice. The animals treated with DSM 33407 exhibit a greater loss of weight compared to the group treated with the placebo.
FIG. 8B shows the efficiency on the loss of weight after a change to a diet less rich in fat in obese mice. The animals treated with DSM 33407 exhibit a greater loss of weight compared to the group treated with the placebo.
FIG. 8C shows the feed efficiency after a change to a diet less rich in fat in obese mice. The feed efficiency was reduced in animals treated with DSM 33407 in comparison with the placebo.

The treatment with DSM 33407 potentiates the loss of weight during a switch to a diet less rich in fat in obese mice as shown in FIG. 8. The switch from an HF60 diet to ND causes a drastic weight loss. Among the animals having switched from an HF60 to an HFD45 diet, the animals treated with DSM 33407 had a greater loss of weight compared to the group treated with the placebo (FIGS. 8A and 8B). The feed efficiency was reduced in animals treated with DSM 33407 in comparison with the placebo (FIG. 8C).

The results thus confirmed that the switch from an HF60 diet to ND causes a drastic weight loss in obese mice. In the obese mice switched onto a diet less rich in fat (HFD45) and treated with DSM 33407, a loss of weight and a decrease in feed efficiency were observed. Despite the switch to the HFD45 diet, the animals having received the placebo continued to gain weight during the 4 weeks of monitoring. These results indicate a potentiating effect of DSM 33407 on the loss of weight in obese animals.

Example 13: Anti-Inflammatory Effect of the Strain According to the Invention During a Diet Allowing the Loss of Weight The study aims to measure the anti-inflammatory effect of DSM33407 on the liver of obese mice during a protocol aimed at making animals lose weight by exposing them to a diet having a reduced fat content by measuring the amount of hepatic cytokines (chemokines) after 4 weeks.

The animal protocol is identical to that of example 8. At the end of the study, the animals were sacrificed and the tissues of interest, here the livers, were immediately removed and frozen while awaiting their analysis. The frozen tissues were transformed in nitrogen powder. The ground materials were then lysed and homogenised cold. After quantification (Bradford), the extracted proteins were diluted and the samples normalised at 1 mg/mL (lysis buffer with 1% Bovine serum Albumin). The assay of the proteins of interest (IL-6 for Interleukin-6, IFNγ for interferon gamma; TNFα for tumour necrosis factor alpha) were made according to the recommendations of the quantification kit manufacturer (BioLegend). The quantification data were analysed by (i) evaluating their distribution (Shapiro-Wilk test), then via (ii) one-way ANOVA with multiple comparison (Dunett) via the Prism9 software (GraphPad). The data are expressed as a mean t standard deviation (MSD) and the significance threshold is set at $p<0.05$ for all analyses. (Statistic symbols on graphs: *$p<0.05$, $p<0.01$, *$p<0.001$, ****$p<0.0001$).

Figure 20:
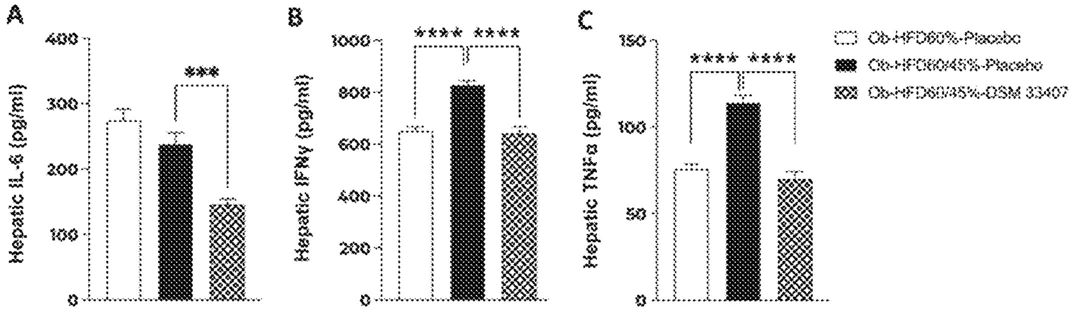
FIG. 20 shows the anti-inflammatory effect of DSM 33407 during a diet leading to loss of weight by measuring the hepatic levels of IL-6 (A), IFNγ (B) and TNFα (C).

The results are shown in FIG. 20. In the group exposed to a diet reduced in fat for 4 weeks and receiving the placebo, there was a significant increase in IFNγ and TNFα. In the group of mice under a diet reduced in fat and receiving DSM 33407, an improvement in hepatic inflammation was observed by the strong reduction of IL-6, IFNγ and TNFα.

Example 14: Effect of the Strain According to the Invention on Adipogenesis in Adipose Tissue The main objective of the study was to evaluate the impact of a treatment with DSM 33407 on the evolution of the weight and body composition of the animals during exposure to a fat-rich diet for 12 weeks.

The study protocol is as follows. A total of thirty (30) male C57Bl6 mice aged 7 weeks were exposed either to a standard diet (ND for normal diet), or to a high fat diet (HFD45: 45% of the calorie intake comes from fats) for 12 consecutive weeks. During this period, the animals were treated daily by oral feeding, either with DSM 33407 (treated group), or with its vehicle (control group). During the study, the weight of the animals was measured and the body composition measurements (fat mass and lean mass) by magnetic resonance were carried out at the end of the study (D84). Each group was composed of 10 mice.

The main objective of the study was to evaluate the impact of a treatment with DSM 33407 on the weight evolution and body composition of the animals during exposure to an obesogenic diet.

The daily weight tracking results were analysed by two-way ANOVA with multiple comparisons (Benjamini, Krieger and Yegutieli test), and the body composition results were analysed by one-way ANOVA with multiple comparisons (Fischer LSD test). All the results are expressed as a mean±standard deviation (MSD) and the significance threshold is set at $p<0.05$ (statistical symbols in the graphs: *$p<0.05$, $p<0.01$, *$p<0.001$).

Figure 9:
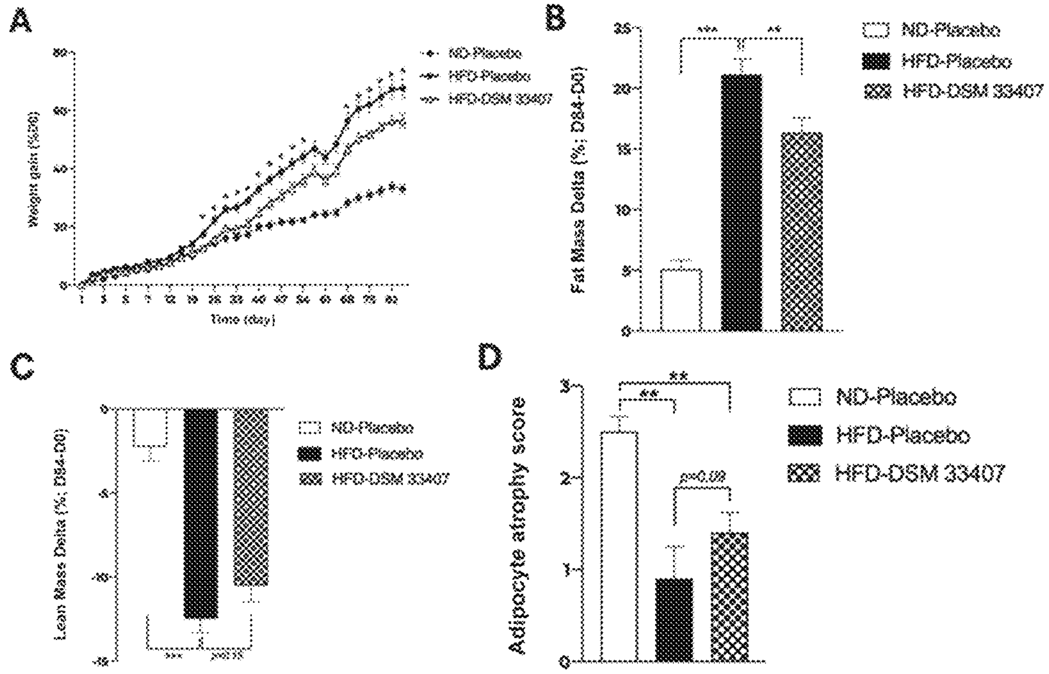
FIG. 9A shows the effect of the treatment on the weight gain and the accumulation of fat. During exposure to an obesogenic diet of HFD45 type, DSM 33407 protects against weight gain.
FIG. 9B shows the effect of the treatment on the weight gain and the accumulation of fat During exposure to an obesogenic diet of HFD45 type, DSM 33407 limits the accumulation of fat.
FIG. 9C shows the effect of the treatment on the weight gain and the accumulation of fat. During exposure to an obesogenic diet of HFD45 type, DSM 33407 has a tendency to limit the lean mass loss associated with the weight gain.
FIG. 9D shows the effect of the treatment on adipocyte hypertrophy. The treatment with DSM 33407 has a strong tendency to prevent visceral adipocyte hypertrophy induced by exposure to an HFD45 diet.

During exposure to the obesogenic diet of HFD45 type, a daily treatment with DSM 33407 protects against weight gain (FIG. 9A) and limits the accumulation of fat mass (FIG. 9B), and has a tendency to limit the lean mass loss associated with the weight gain (FIG. 9C).

A very significant increase in adipocyte hypertrophy (reduction of atrophy) was also observed in animals placed under HFD45 and treated with the placebo. On the other hand, the treatment with DSM 33407 has a strong tendency to prevent visceral adipocyte hypertrophy induced by exposure to an HFD45 diet (FIG. 9D).

The animals under HFD45 all gained significantly more weight than the animals that remained under ND. The treatment with DSM 33407 significantly prevented the weight gain and visceral adipocyte hypertrophy. At the end of the study, body composition analysis showed that in these animals the accumulation of fat mass was also significantly reduced compared to animals under placebo. The DSM 33407 treatment also had a strong tendency to limit the loss of lean mass associated with the induction of obesity by a fatty diet.

Example 15: Effect of the Strain According to the Invention on Adipogenesis in Adipose Tissue (Leptin)

The study protocol is as follows. A total of thirty (30) male C57Bl6 mice aged 7 weeks were exposed either to a standard diet (ND for normal diet), or to a high fat diet (HFD45: 45% of the calorie intake comes from fats) for 12 consecutive weeks. During this period, the animals were treated daily by oral feeding, either with DSM 33407 (treated group), or with its vehicle (control group). At the end of the study, the animals were fasting and blood was taken in order to extract the plasma therefrom and measure the levels of leptin. These measurements were carried out with custom built Biorad plates (Biorad, Mames Ia Coquette, France). All the samples were evaluated in duplicate. The results were analysed by one-way ANOVA with multiple comparisons (Benjamini, Krieger and Yegutieli test) using the Prism8 software (Graphpad). All the results are expressed as a mean±standard deviation (MSD) and the significance threshold is set at $p<0.05$ for all analyses (statistic symbols in the graphs: *$p<0.05$, *$p<0.01$, ***$p<0.001$).

Figure 10:
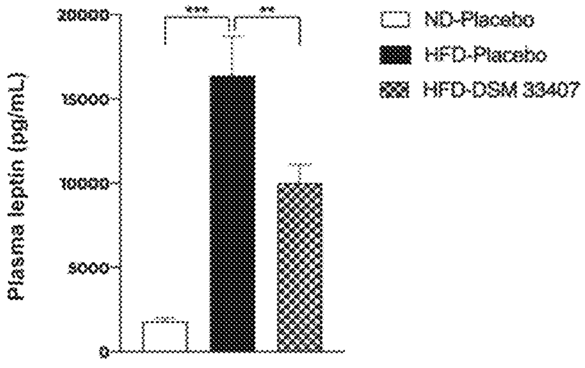
FIG. 10 shows the effect of the treatment on the levels of leptin. DSM 33407 made it possible to prevent the increase in circulating leptin (A) levels typically observed after 12 weeks of exposure to HFD45. Leptin is in particular a hormone produced by adipose tissue (adipocytes), depending on the volume of the fat tissue and is a marker of adiposity.

A daily treatment with DSM 33407 made it possible to prevent the increase in circulating leptin levels (FIG. 10A) typically observed after 12 weeks of exposure to HFD45.

The exposure to a fat-rich diet thus causes a very significant increase in the levels of leptin circulating in the animals under placebo. In the group of animals treated daily with DSM 33407, this increase was significantly reduced for leptin.

Example 16: Effect of the Strain According to the Invention on the Compulsive Food Behaviours (Anorexigenic Effect)

The objective of this study was to evaluate the capacity of DSM 33407 to affect the food behaviour of animals subjected to an obesogenic diet. To do so, a fasting paradigm followed by re-exposure to food was used, in order to induce reactive hyperphagia in animals.

The study protocol is as follows. A total of twenty (20) male C57Bl6 mice aged 7 weeks were exposed to a high fat diet (HFD45: 45% of the calorie intake comes from fats) for 2 consecutive weeks. During this period, the animals were treated daily by oral feeding, either with DSM 33407 (treated group), or with its vehicle (control group). On the 14$^{th}$ day, the animals were weighed and made to fast for 12 h. In the morning of the 15$^{th}$ day, the feeders were placed in the cages. Then the food intake of the animals was measured after 1, 2, 4, 8, 24, 48, and 72 h. The animals were weighed once a day. The results were analysed by two-way ANOVA with multiple comparisons (non-corrected LSD test) using the Prism8 software (Graphpad). All the results are expressed as a mean±standard deviation (MSD) and the significance threshold is set at $p<0.05$ for all analyses (statistic symbols in the graphs: *$p<0.05$).

Figure 11:
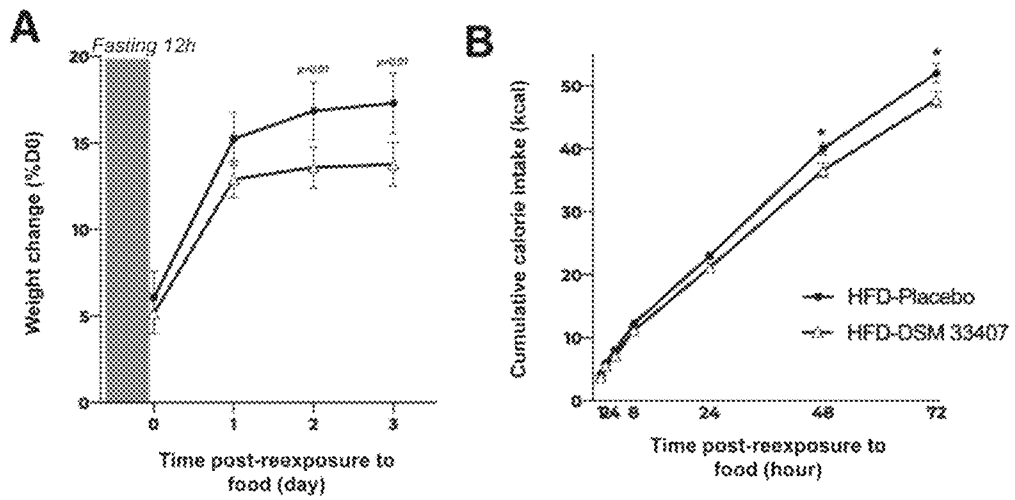
FIG. 11A shows the effect on compulsive food behaviours. DSM 33407 induces a strong tendency to reduce the body weight uptake (FIG. 11A).
FIG. 11B shows the effect on compulsive food behaviours. DSM 33407 induces a strong tendency to reduce the reaction hyperphagia induced following a fasting of 12 h.

In animals subjected to a fat-rich diet (HFD45), fasting for 12 h induces a loss of weight. On re-exposure to food the animals rapidly regain a lot of weight and exhibit a reaction hyperphagia. The animals treated daily with DSM 33407 have a strong tendency to reduce body weight uptake (FIG. 11A) visible from 48 h. In parallel, the amount of calories ingested (cumulative) during the phase of hyperphagia induced by fasting was reduced in the group treated with DSM 33407 (FIG. 11B).

Example 17: Effect of the Strain According to the Invention on the Plasma Glucose Levels and on Hepatic Glycolysis The study protocol for the plasma glucose level is as follows. A total of thirty (30) male C57Bl6 mice aged 7 weeks were exposed either to a normal diet (ND for normal diet; 10 mice) or to a high fat diet (HFD45, 45% of the calorie intake comes from fats) for 4 consecutive weeks (20 mice). During this time, the animals were treated daily by oral feeding, either with DSM 33407 (treated group), or with its vehicle (control group). Each group was composed of 10 mice. During the study, the animals were fasting and blood was taken in order to extract the plasmas from them at different times (0 and 4 weeks). The circulating glucose levels were measured using custom built BIORAD plates (Biorad, Mames Ia Coquette, France). All the samples were evaluated in duplicate. The results were analysed by one-way ANOVA with multiple comparisons (Benjamini, Krieger and Yegutieli test) using the Prism8 software (Graphpad). All the results are expressed as a mean±standard deviation (MSD) and the significance threshold is set at $p<0.05$ for all analyses (statistic symbols in the graphs: ***$p<0.001$).

Figure 12:
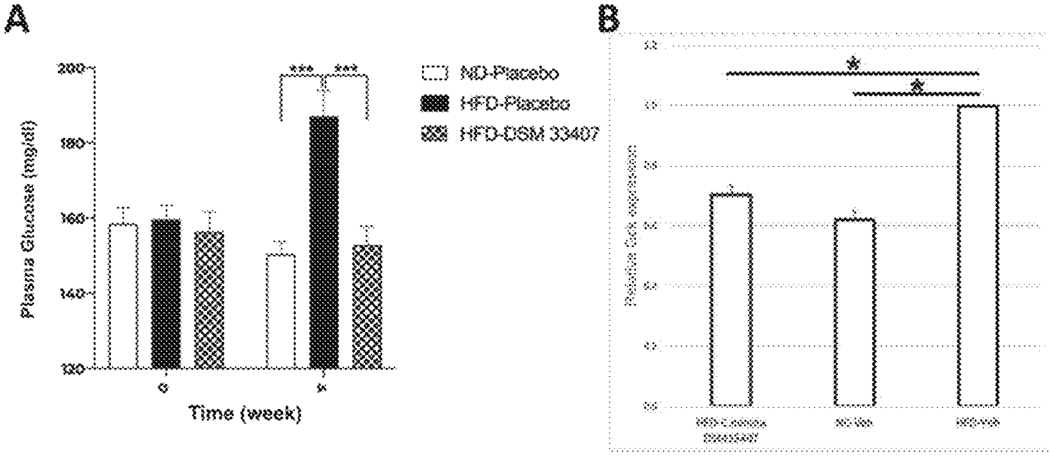
FIG. 12A shows the effect of a daily treatment with DSM 33407 on the increase in fasting plasma glucose levels conventionally observed during exposure to an HFD45 diet for 4 weeks.
FIG. 12B shows the gene expression level of the glucokinase (Gck) gene relative to the HFD-Veh control group not having received treatment and therefore the effect on hepatic glycolysis.

The exposure to a fat-rich diet for 4 weeks induced a very significant increase in the fasting plasma glucose levels in the animals under placebo shown in FIG. 12A. In the group of animals treated daily with DSM 33407, this increase was totally avoided.

The study protocol for hepatic glycolysis is identical to that previously described. In addition, the expression of glucokinase (Gck) was measured by quantitative PCR using a pair of specific primers (Bio-Rad). Briefly, the RNAs were extracted from the livers of mice according to and with the RNeasy Lipid tissue kit by Qiagen. The synthesis of the complementary DNAs was carried out with the iScript Advanced cDNA synthesis kit by Bio-Rad, according to the instructions. Finally, from the cDNA, quantitative PCR was carried out using the SsoAdvanced Universal SYBR Green Supermix kit by Bio-Rad, according to the instructions with the device CFX 96 Touch by Bio-Rad. The pairs of primers used for this study (Gck, Gapdh, Tbp1, Hrpt) are pairs designed and validated by Bio-Rad. All the data used for the statistical analysis were extracted via the CFX Maestro software by Bio-Rad. The statistical analysis was carried out with R (v. 3.6.2). An ANOVA was carried out with the processing factor followed by a Tukey post-hoc test making it possible to obtain a value of p adjusted to the multiple comparison.

The animals subjected to a fat-rich diet (HFD-Veh) developed an overexpression of the glucokinase gene (Gck), a key regulator of the hepatic glycolysis, relative to the control group (NC-Veh). The treatment with *C. minuta* DSM 33407 (HFD-DSM 33407) totally inhibits Gck overexpression induced by the fat-rich diet. Therefore, it can be concluded that *C. minuta* DSM 33407 acts on hepatic metabolism through regulation of the energy pathways in order to prevent the accumulation of lipids (FIG. 12B).

Example 18: Effect of the Strain According to the Invention on the Bile Acid Balance The study protocol is identical to that presented in example 5. In the context of this study, the dose of *C. minuta* DSM 33407 of $10^9$ CFU was used. The bile acids were measured from a sample of serum collected on day 40 (D40) by a HPLC (High Performance Liquid Chromatography) method.

Figure 13:
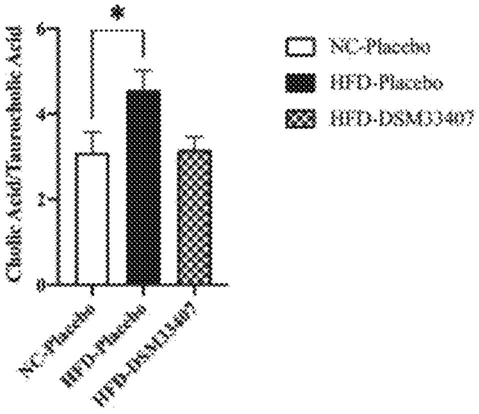
FIG. 13 shows the effect on the bile acid balance, in particular the effect of DSM 33407 on the ratio of cholic acid (CA) to taurocholic acid (TCA) circulating after 6 weeks under a control (NC) or fatty (HFD) diet.

The bile acids play a predominant role in intestinal absorption of lipids. The bile acids are secreted by the liver in the bile in the form of conjugated acids, among which taurocholic acid (TCA) is the main component in mice. TCA is then unconjugated by the bacteria of the intestinal microbiota to form cholic acid (CA). 95% of the bile acids secreted by the bile are reabsorbed in the small intestine during digestion, which forms the enterohepatic cycle of the bile acids. The circulating CA/TCA ratio is therefore an indicator of the activity of the enterohepatic cycle and reflects the metabolic equilibrium of the liver and the microbiota. When the animals are fed for 6 weeks with a fat-rich diet, the CA/TCA ratio is increased significantly (FIG. 13). This imbalance is totally avoided by the treatment with *C. minuta* DSM 33407, which indicates that the treatment is effective for treating diseases related to a bile production disorder such as biliary stones and other bile duct pathologies such as primitive sclerosing cholangitis.

Example 19: Effect of the Strain According to the Invention on the Bile Acid Cycle The test aims to study the impact of DSM33407 on the bile acid cycle during a protocol for inducing obesity by a fatty diet via the level of expression (mRNA) of the bile acid receptors in the liver and of endocrine hormones of the digestive tract (illeum) sensitive to bile acids.

The study protocol for the animal part is identical to that of example 6. At the end of the study, the animals were sacrificed and the tissues of interest, here the livers and ileons, were immediately removed and frozen while awaiting their analysis.

The messenger RNA extraction was carried out by means of Rneasy Plus (Qiagen) kits, the complementary DNAs generated by the negative transcription (iScript Advanced cDNA synthesis, Bio-Rad) and the amplification carried out by real-time quantitative PCR (SsoAdvanced SYBR Green Universal Supermix (Bio-Rad). Specific primers of the genes of interest (Tgr5 for G-protein coupled bile acid receptor, Fxr for famesoid X receptor, Fgf15 for Fibroblast growth factor 15) had been developed and validated beforehand (Bio-Rad). The experiment is carried out in triplicate. The PCR cycle data were analysed by (i) evaluating their distribution (Shapiro-Wilk test), then via (ii) one-way ANOVA with multiple comparison (Dunett) via the Prism9 software (GraphPad). The data are expressed as a mean±standard deviation (MSD) and the significance threshold is set at $p<0.05$ for all analyses. (Statistic symbols on graphs: *$p<0.05$, $p<0.01$, *$p<0.001$, ***$p<0.0001$).

Figure 21:
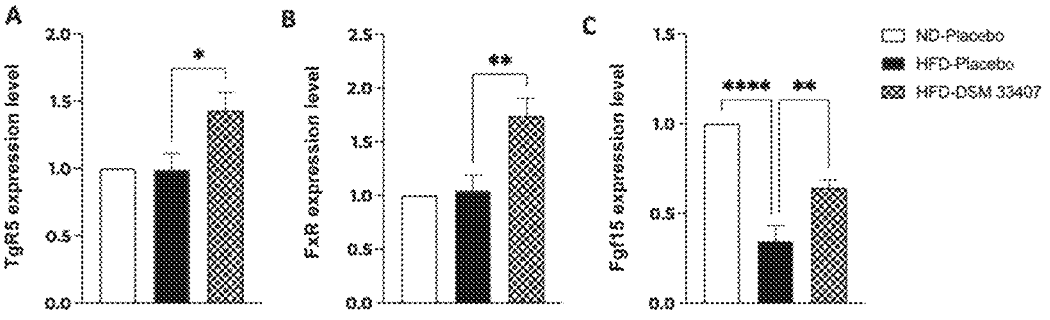
FIG. 21 shows the impact of DSM33407 on the bile acid cycle during an obesity induction protocol by measuring the hepatic expression level of TgR5 (A) and of FxR (B) and the level of ileal expression of Fgf15 (C).

The results are shown in FIG. 21. For the animals receiving the placebo, exposure to a fatty diet did not have an effect on the levels of expression of Tgr5 and Fxr in the liver, but induced a strong reduction in Fgf15 in the ileum. Conversely, the animals under DSM 33407 showed strong increases for the 3 markers monitored.

Example 20: Effect of the Strain According to the Invention on the Liver Function The test aims to study the protective effect of DSM33407 on the liver function during a protocol for inducing obesity by a fatty diet via the expression level (mRNA) of proteins involved in the metabolism of hepatic lipids.

The study protocol is as follows. Thirty (20) male C57Bl6 mice aged 7 weeks were exposed to a high fat diet (HFD: 45% of the calorie intake comes from fats) for 12 consecutive weeks. During this period, the animals were treated daily by oral feeding, either with DSM 33407 (treated group), or with a vehicle (placebo; control group). At the end of the study, the animals were sacrificed and the tissues of interest, here the livers, were immediately removed and frozen while awaiting their analysis.

The messenger RNA extraction was carried out by means of Rneasy Plus (Qiagen) kits, the complementary DNAs generated by the negative transcription (iScript Advanced cDNA synthesis, Bio-Rad) and the amplification carried out by real-time quantitative PCR (SsoAdvanced SYBR Green Universal Supermix (Bio-Rad). Specific primers of the genes of interest (Fasn for fatty acid synthase, Cd36 for fatty acid translocase Cd36) had been developed and validated beforehand (Bio-Rad). The experiment is carried out in triplicate. The PCR cycle data were analysed by (i) evaluating their distribution (Shapiro-Wilk test), then via (ii) one-way ANOVA with multiple comparisons (Dunett) via the Prism9 software (GraphPad). The data are expressed as a mean±standard deviation (MSD) and the significance threshold is set at $p<0.05$ for all analyses. (Statistic symbols on graphs: *$p<0.05$, $p<0.01$, $p<0.001$, ****$p<0.0001$).

Figure 22:
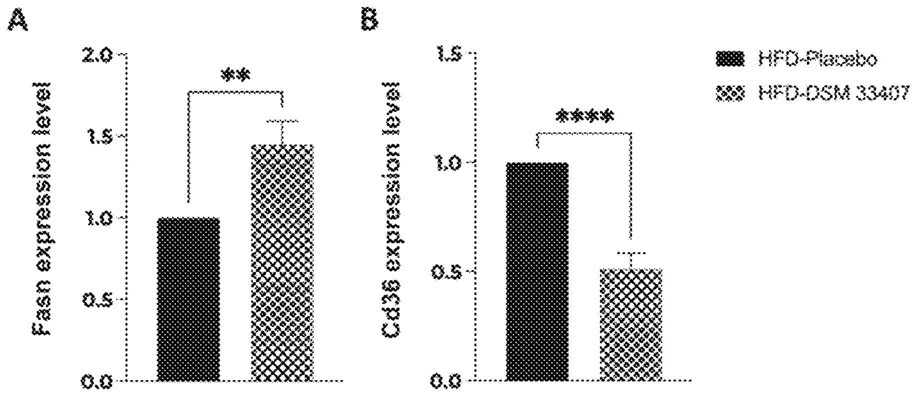
FIG. 22 shows the protective effect of DSM33407 on the hepatic function during a protocol for inducing obesity by a fatty diet by measuring the expression level of Fasn (A) and Cd36 (B).

The results are shown in FIG. 22. The treatment of the animals with DSM 33407 over 12 weeks in parallel with exposure to a fatty diet made it possible to significantly increase the levels of expression of Fasn and decrease the expression of Cd36.

Figure 14A:
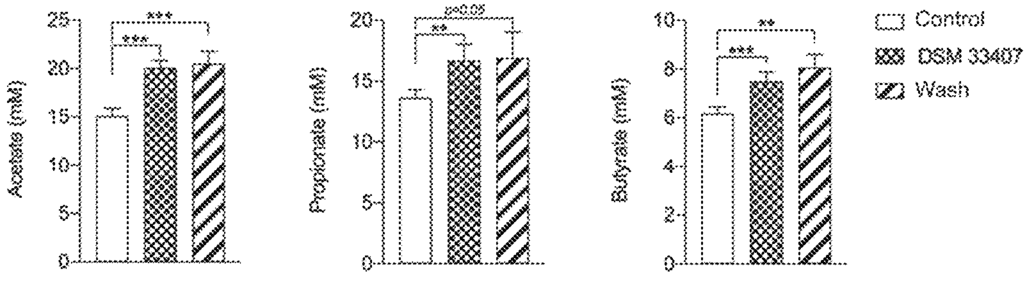
FIG. 14A shows the beneficial effect of DSM 33407 on an obese human microbiota. DSM 33407 induces a significant and persistent increase of the synthesis of SCFA (short-chain fatty acids) (acetate, propionate, and butyrate).
Figure 14B:
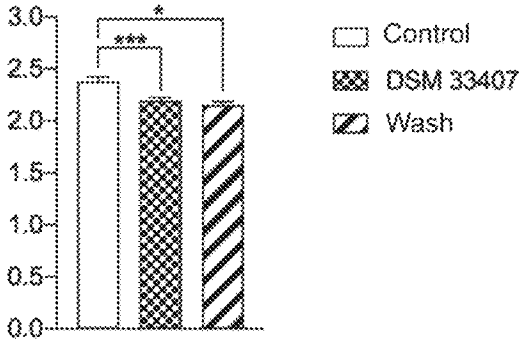
FIG. 14B shows the beneficial effect of DSM 33407 on an obese human microbiota. DSM 33407 induces a significant and persistent reduction of the synthesis of BCFA (branched-chain fatty acids).

Example 21: Effect of the Strain According to the Invention on the Microbiota of Obese Human Subjects The study protocol is as follows. SHIME® (Simulator of Human Intestinal Microbial Ecosystem) is a validated in vitro system for studying the biodistribution DSM 33407 and its impact on the microbiota. It consists of a succession of 5 reactors simulating the various parts of the human gastrointestinal tract. The microbiotes of 2 obese human subjects were isolated from the faeces of preselected donors for their lack of Christensenellaceae and injected into the SHIME system. After 4 weeks of stabilisation of the microbiota and of controls, the DSM 33407 treatment was inoculated for 3 weeks ($2 \cdot 10^9$ CFU/day). Finally, a period of washing (without treatment) of a week was carried out at the end of the treatment in order to evaluate the presumed persistence of the effect of the product. The production of SCFA (short-chain fatty acid; acetate, propionate, butyrate) and SCFAr (branched SCFA, isobutyric acid, isovaleric acid and isocaprylic acid) were measured throughout the study (FIGS. 14A and 14B). The results were analysed by one-way or mixed model ANOVA or with multiple comparisons (non-corrected Fischer LSD test) using the Prism8 software (Graphpad). All the results (FIGS. 14A and 14B) are expressed as a mean±standard deviation (MSD) and the significance threshold is set at $p<0.05$ for all analyses (statistic symbols on graphs: *$p<0.05$, $p<0.01$, *$p<0.001$).

Figures 14C, 14D:
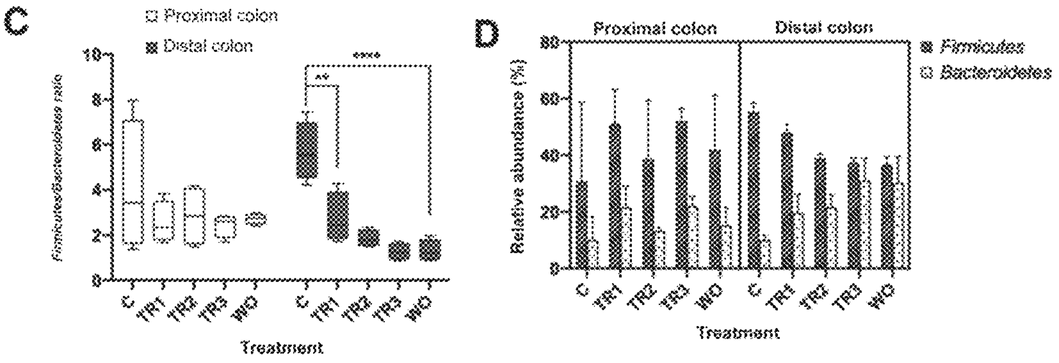
FIG. 14C shows the effect of DSM 33407 on the Firmicutes/Bacteroidetes ratio in the distal colon.
FIG. 14D shows the effect on the relative abundance of Firmicutes and the increase in Bacteroidetes.

Samples were taken in the system throughout the study in order to be able to monitor the evolution of the composition of the inoculated microbiotes in response to the treatment with DSM 33407 (FIGS. 14C and 14D).

The DNA of samples of the microbiota was extracted with a specific kit. All the results are expressed as a mean±standard deviation (MSD) and the significance threshold is set at $p<0.05$ for all analyses (statistic symbols in the graphs: *$p<0.05$, $p<0.01$, $p<0.001$).

The results presented in FIG. 14 make it possible to show the beneficial effects of a daily treatment with DSM 33407 on the microbiota of an obese human. Indeed, a significant, rapid and lasting increase of the levels of the main 3 SCFA (Short Chain Fatty Acids) (acetate, propionate, butyrate) measured in the proximal colon was noted (FIG. 14A). The production of these SCFA reflects an increase in the beneficial saccharolytic fermentation activities in the distal colon (FIG. 14B). In parallel, a significant and lasting reduction of the levels of BCFA (Branched Chain Fatty Acids) was measured. The production of BCFA indicates a reduction in proteolytic activities within the treated microbiota. It is interesting to note that, during the washing period, the levels of SCFA and BCFA remained at their level without returning to the initial concentrations. This suggests the establishment of long-term persistent beneficial effects of DSM 33407 after the treatment is stopped.

The results presented in FIGS. 14C and 14D show a significant decrease in the Firmicutes/Bacteroidetes ratio in the distal colon observed when DSM 33407 was inoculated (TR1, TR2 and TR3). This effect remained constant after a week without inoculation of the bacterium. The reduction in this ratio is explained by the decrease in the relative abundance of Firmicutes and the increase in Bacteroidetes (Figure D). These results thus show the beneficial effect of DSM 33407 in the recovery of healthy microbiota of obese individuals. In fact, the Bacteroidetes/Firmicutes ratio is known to be reduced in obese individuals or those suffering from inflammatory diseases of the intestine.

Example 22: Effect of the Strain According to the Invention on the Beneficial Bacteria of the Microbiota and on the Diversity of the Intestinal Microbiota in Animals The study protocol is identical to that presented in example 5.

Study of Beneficial Bacteria.

The composition of the microbiota was obtained by the shotgun sequencing method. The extraction of DNA from the mouse stool samples was carried out using the DNeasy Power Soil Pro Kit from Qiagen and according to the protocol recommended by the manufacturer. The extracted DNA samples were quantified using a Qubit 4 fluorometer and the Qubit™ dsDNA HS Kit (Thermofisher Scientific) test. DNA libraries were prepared using the Nextera XT library preparation kit (Illumina) and Nextera Index Kit (Illumina) according to the manufacturer's protocol. DNA libraries were quantified using a Qubit 4 fluorometer and the Qubit™ dsDNA HS test kit. Pairwise sequencing (2×150 bp) was carried out on Illumina HiSeq4000 with an average sequencing depth of 5 million reads.

The sequence processing was carried out using the CosmosID "Metagenomics Cloud" online platform. The data annotated at the family rank were exported, then the statistical analyses were carried out in Python 3.

Figure 15A:
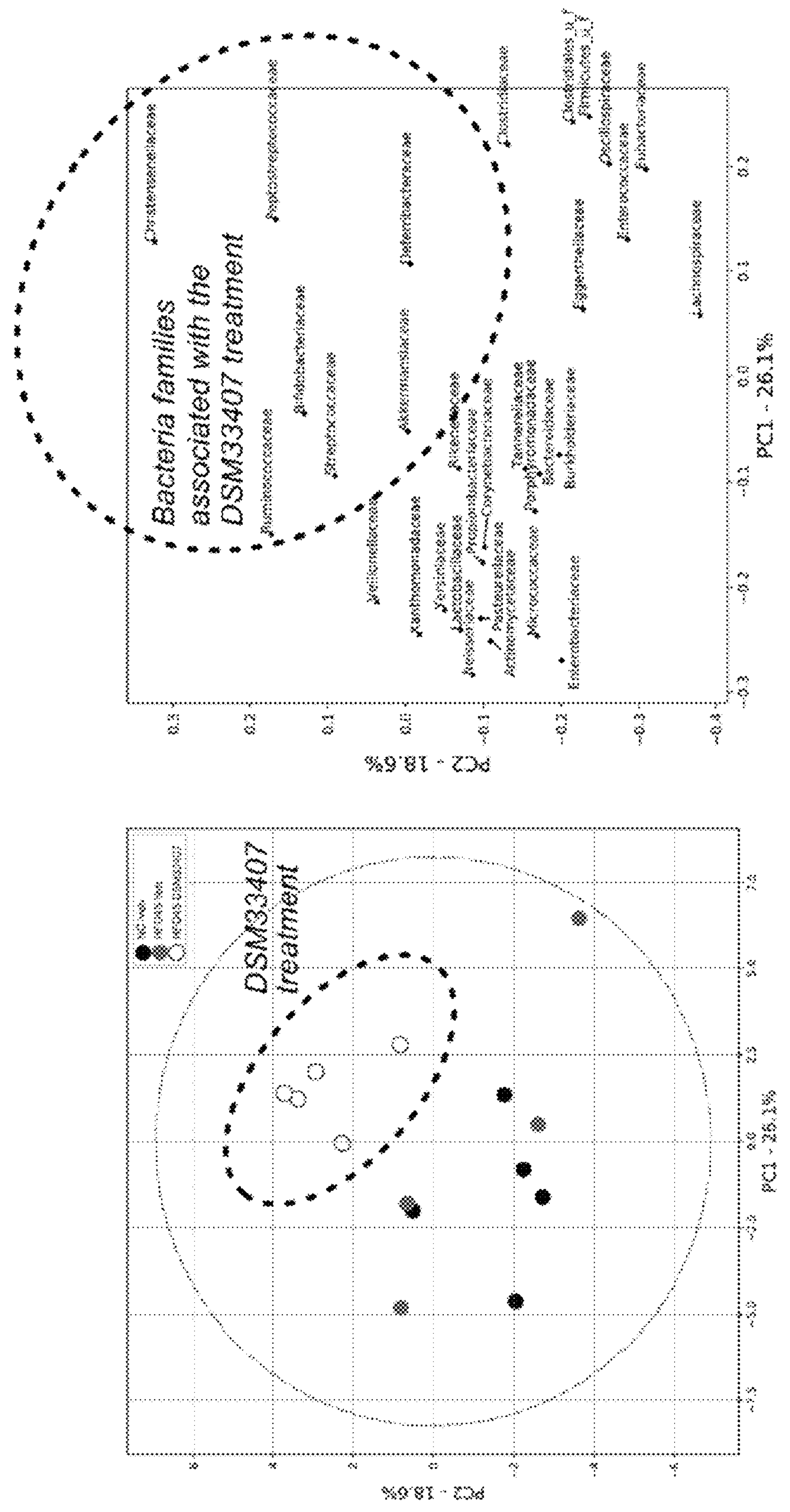
FIG. 15A shows the composition of the metagenome in murine faecal samples (A).

The data were analysed by Principal Component Analysis in order to identify groups without a priori and presented in FIG. 15A.

Treatment based on *C. minuta* DSM 33407 supports the development of other bacteria such as the Bifidobacteriaceae and the Ruminococcaceae known for their beneficial metabolism, respectively production of lactic acid and butyric acid, indicating a beneficial effect on the intestinal microbiota.

Study of the Diversity of the Microbiota.

The non-supervised hierarchical classification was obtained by using a Python 3 script using the clustermap function of the Seaborn library v.0.10.1. The function calculates the matrix of Euclidean distances between the families of bacteria and then the classes using the Voor Hees algorithm. The matrix is coloured according to the correlation parameter "r".

Figure 15B:
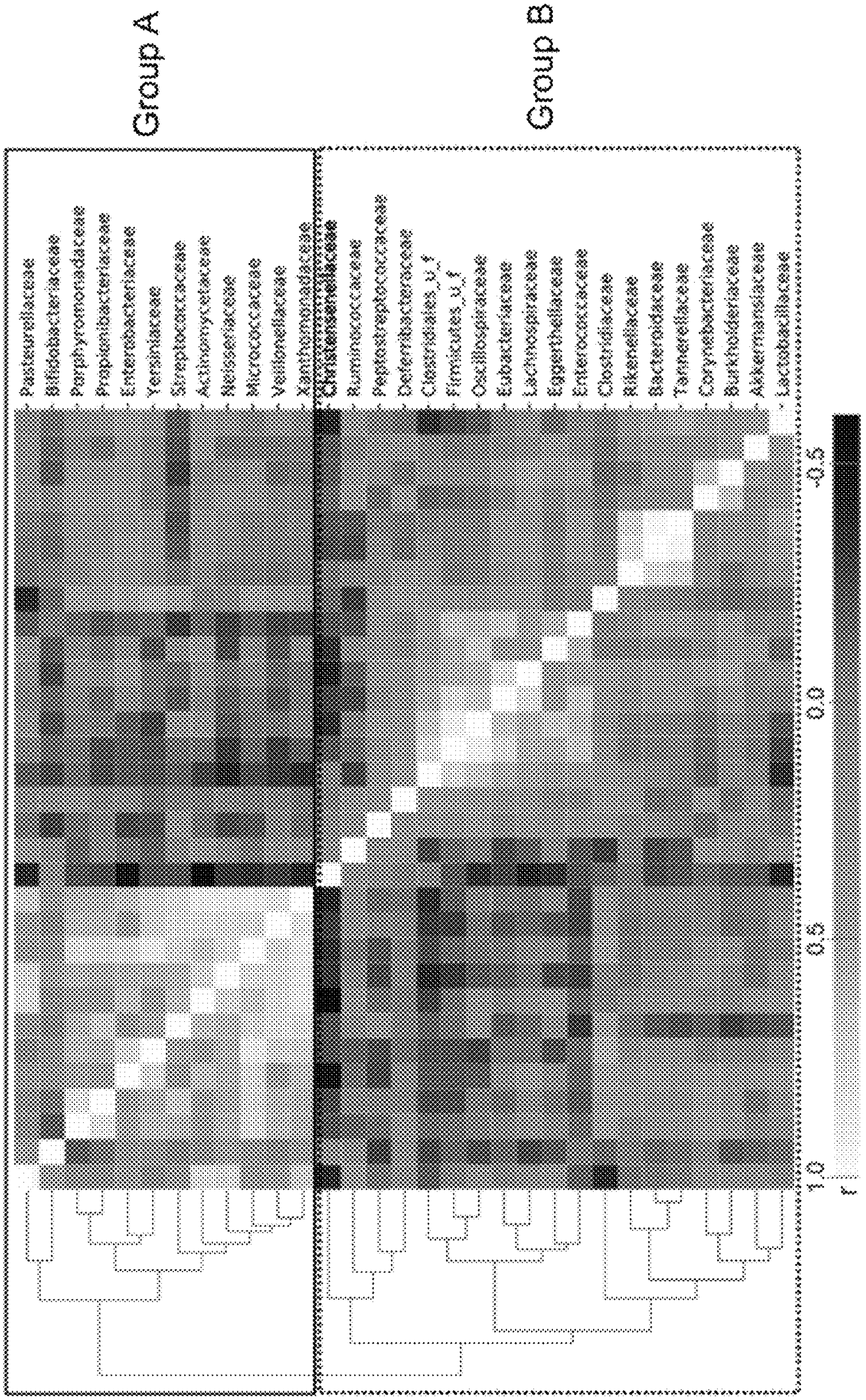
FIG. 15B shows the unsupervised hierarchical classification of the mouse metagenome after 8 weeks of a fat-rich diet and with or without treatment with the bacterium DSM 33407.

The results are presented in FIG. 15B and shows that the mice treated for 8 weeks with a diet rich in fat and supplemented or not with DSM 33407 promotes the families of beneficial bacteria, such as the Ruminococcaceae, the Rikenellaaceae, the Lactobacillaceae and the Akkermansiaceae (Group B). In contrast, families of bacteria rich in opportunistic pathogens such as the Enterobacteriaceae, the Yersineaceae, the Neisseraceae and the Xanthomonaceae (Group A) are grouped far away from the group supported by the Christensenellaceae.

Example 23: Effect of the Strain According to the Invention on the Activity of the Intestinal Microbiota in Animals The study aims to show the impact of daily boost with DSM33407 on the activity of the intestinal microbiota of the animal during a protocol for inducing obesity by a fatty diet by quantifying certain short chain fatty acids (SCFA) present in the caecum.

The study protocol is as follows. Thirty (30) male C57Bl6 mice aged 7 weeks were exposed either to a standard diet (ND for normal diet), or to a high fat diet (HFD: 45% of the calorie intake comes from fats) for 12 consecutive weeks. During this period, the animals were treated daily by oral feeding, either with DSM 33407 (treated group), or with a vehicle (placebo; control group). At the end of the study, the animals were sacrificed and the tissues of interest, here the colon including the caecum, were immediately removed and frozen while awaiting their analysis.

The caeca were homogenised (Precellys), filtered twice (0.2 μm, 1 h, 15° C. and 10,000 g, then 10 kDa, 1 h, 15° C. and 10,000×g. The filtrates were mixed with the various elements making it possible to quantify by nuclear magnetic resonance (NMR), i.e. of DSS-d6 (internal standard), DFTMP (pH indicator), and D20 (spin-lock NMR). Controls not containing caecal samples were carried out. The solutions were transferred into dedicated tubes (3 mm SampleJet) and then passed into the auto-sampler (SampleJet) awaiting NMR analyses (Avance 600 Mhz NMR, Bruker, noesygppr1). The NMR data were analysed (Chenomx NMR 8.6), then the quantities of SCFA of interest, Acetate, Butyrate, and Propionate, were reported relative to the volume and to the weight of the initial samples. The SCFA quantification data were analysed by (i) evaluating their distribution (Shapiro-Wilk test), then via (ii) one-way ANOVA with multiple comparisons (Dunett) via the Prism9 software (GraphPad). The data are expressed as a mean±standard deviation (MSD) and the significance threshold is set at $p<0.05$ for all analyses. (Statistic symbols on graphs: *$p<0.05$, $p<0.01$, *$p<0.001$, ****$p<0.0001$)

Figure 23:
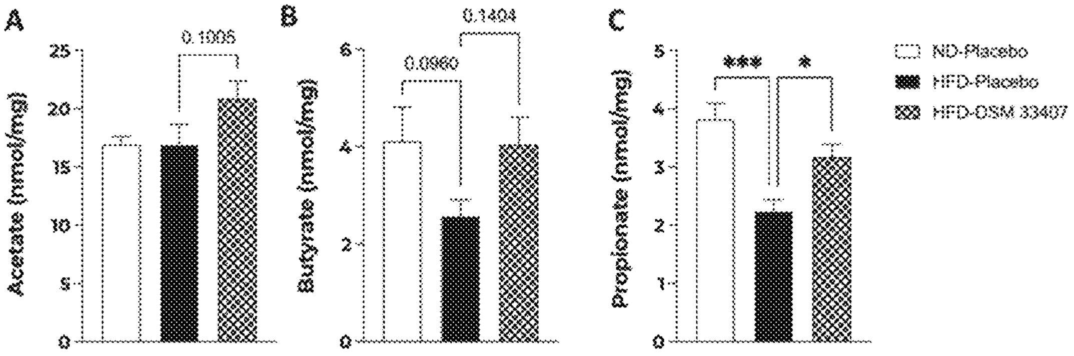
FIG. 23 shows the impact of daily boost with DSM33407 on the activity of the intestinal microbiota of the animal during a protocol for inducing obesity by a fatty diet by measuring the concentration of acetate (A), butyrate (B) and propionate (C) in faeces.

The results are shown in FIG. 23. Exposure to a fat-rich diet for 12 weeks resulted in a reduction in the levels of butyrate and propionate in the caeca of animals under placebo. No effect of the diet was observed on the acetate levels. The treatment with DSM 33407 made it possible to significantly increase the levels of acetate and maintain normal levels of butyrate and propionate.

Example 24: Anti-Inflammatory Effect of the Strain According to the Invention The study protocol is as follows. The HCT-116 and HepG2 cell lines were obtained from Sigma-Aldrich. The HCT-116 were maintained in culture in McCoy's 5A medium (Gibco) supplemented with 10% of foetal calf serum (Gibco) and 1% of penicillin/streptomycin (Sigma-Aldrich) and the HepG2 were cultivated in DMEM medium (Gibco) supplemented with 10% of FCS (Gibco), in an incubator in a humid atmosphere at 37° C. and 5% of $CO_2$.

The cells were seeded at a density of 10,000 cells/well in a total is volume of 100 μl in a 96-well plate. After 24 h of incubation, the culture medium was removed from the adherent cells and new medium supplemented with 10% of supernatant in stationary phase of DSM 33407 was added and in GAM control (bacterial culture medium). The Akt inhibitor VIII was used as positive control. Each condition was made in 4 replicates. The cells were incubated for an additional 48 h or 72 h.

Cell proliferation was determined by the use of the CellTiter-Glo 2.0 assay (Promega). The measurements were carried out according to the manufacturer's instructions. Briefly, the plates were removed from the incubator and left to balance at room temperature for 30 min and an equal volume of CellTiter-Glo 2.0 reagent was added directly to the wells (100 μl). The plates were stirred at 300 rpm for 2 min using a rotary stirrer, then incubated at room temperature for 10 min. The reaction mixture was then transferred into a 96-well white wall plate and the luminescent signal was measured using a microplate reader (FLUOstar Omega, BMG Labtech).

Figure 16:
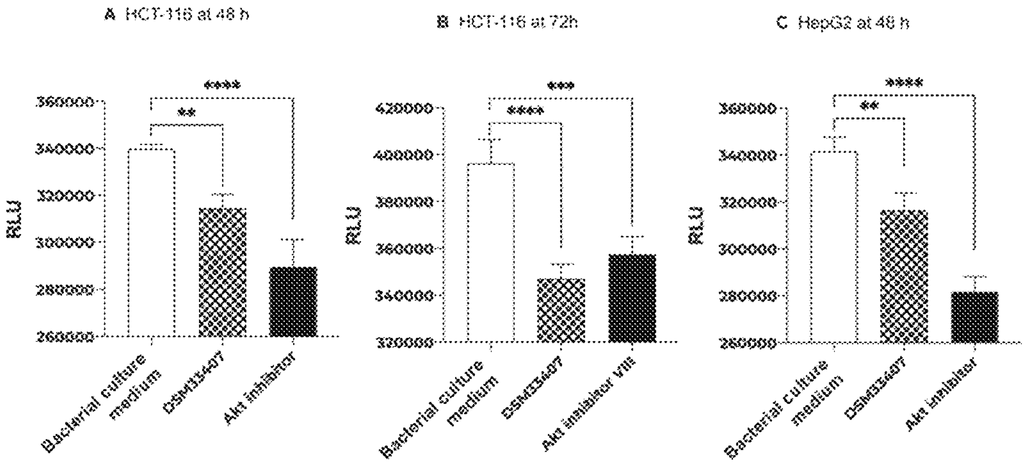
FIG. 16A shows the anti-proliferative effect of DSM 33407 (48 h) on HCT-116 cells (colon adenocarcinoma).
FIG. 16B shows the anti-proliferative effect of DSM 33407 (72 h) on HCT-116 cells (colon adenocarcinoma).
FIG. 16C shows the anti-proliferative effect of DSM 33407 on HepG2 (hepatocarcinoma) cells.

The results presented in FIG. 16 make it possible to observe the influence of the DSM 33407 strain on the proliferation of tumour cells, in particular the effect on a human colon adenocarcinoma cell line, the HCT-116 line, and on a human hepatocyte line, the HepG2 line. The effect of the supernatant on the proliferation was evaluated at 48 h (A) and 72 h (B) on the HCT-116 cells and at 48 h (C) on HepG2. The DSM 33407 supernatant significantly reduces the proliferation relative to the control, corresponding to the cells treated with the bacterial culture medium (bacterial culture medium vs DSM 33407: $p=0.0049$ (A), $p<0.0001$ (B) and $p=0.0019$ (C), Dunnett's multiple comparisons test). The Akt inhibitor VIII is used as control of cell proliferation blocking.

The supernatant of the DSM 33407 strain induces a decrease in the proliferation of HCT-116 and HepG2 tumour lines, suggesting a potential role in the inhibition of tumour development.

The invention claimed is:

1. A composition in the form of a powder, microencapsulated powder, gel capsule, capsule, tablet, pellet, granule, emulsion, suspension, suppository or syrup, said composition comprising at least one pharmaceutically acceptable excipient and one or more of the following:

bacterial cells of *Christensenella minuta* bacterial strain with deposit number DSM 33407;

bacterial cells comprising a 16S rRNA having at least 99.9% sequence identity to 16S rRNA of said bacterial strain; or any combination thereof;

and wherein said bacterial cells are living, dead, attenuated or inactivated.

2. The composition according to claim 1, wherein the composition further comprises a probiotic.

3. The composition according to claim 1, wherein the composition is in solid, liquid or lyophilised form.

4. The composition according to claim 1, wherein said composition is in a form suitable for oral, nasal, parenteral, rectal, sublingual, ocular, auricular, inhaled or cutaneous administration.

5. The composition according to claim 1, wherein at least 50% of said bacterial cells are living bacterial cells of *Christensenella minuta* bacterial strain with deposit number DSM 33407.

6. A food product, a beverage, a nutraceutical, a food additive, a food supplement, a medicament or a dairy product comprising the composition of claim 1.

7. A method of administering the composition of claim 1 to a subject, wherein the method comprises administering the composition to the subject in need of prevention and/or treatment of dysbiosis of the microbiota.

8. A method of administering the composition of claim 1 to a subject, wherein the method comprises administering the composition to the subject in need of prevention and/or treatment of chronic diseases.

9. The bacterial strain, supernatant or A method of administering the composition of claim 7 to a subject, wherein the method comprises administering the composition to the subject in need of prevention and/or treatment of obesity.

10. A method of administering the composition of claim 7 to a subject, wherein the method comprises administering the composition to the subject in need of prevention and/or treatment of metabolic diseases.

11. A method of administering the composition of claim 1 to a subject, wherein the method comprises administering the composition to the subject who has one or more of the following diseases:

a metabolic disease selected from non-insulin-dependent diabetes, gestational diabetes, nonalcoholic steatohepatitis (NASH), hepatic steatosis, pancreatic steatosis, hyperlidemia, hypercholesterolemia, infertility linked to excess weight, or urinary incontinence linked to excess weight, thyroiditis, a cardiac and vascular disease selected from atherosclerosis, thrombopathies, acute pericarditis and chronic constrictive pericarditis, arterial hypertension, or vasculitis, a liver and bile duct disease selected from hepatitis, primary biliary cirrhosis, primary sclerosing cholangitis, cirrhosis, hepatic encephalopathy, or vesicular lithiasis, a joint disease linked to excess weight and selected from osteopenia, osteoporosis, osteoarthritis, or vertebral disc inflammation, a neurodegenerative disease, selected from Alzheimer's disease, Parkinson's disease, motor neuron diseases such as amyotrophic lateral sclerosis, primitive lateral sclerosis, or Kennedy disease, a cancer linked to metabolism and/or to dysbiosis of the microbiota and selected from hepatocarcinomas, gastrointestinal tract cancers such as oesophageal, stomach and colorectal cancer, pancreatic carcinoma, neuroendocrine tumours (NETs) of the gastrointestinal-pancreatic system, hepatic tumours, gallbladder and bile duct tumours, renal tumours, glioblastoma, lymphoma, multiple myeloma, chronic myeloid leukaemia, chronic myeloproliferative diseases, or lung carcinoma, an auto-immune disease, selected from insulin-dependent diabetes, rheumatoid arthritis, ankylosing spondylitis, psoriatic arthritis, systemic lupus erythematosus, or polyendocrine autoimmune syndrome, an atopic skin disease, selected from eczema, or psoriasis, a chronic inflammatory bowel disease, selected from Crohn's disease, hemorrhagic ulcerative rectocolitis, diverticulitis, oesophagitis, gastritis, pancreatitis, gastrointestinal ulcers, or irritable bowel syndrome, a respiratory function disease selected from asthma, cystic fibrosis, chronic obstructive pulmonary disease, interstitial lung diseases and pulmonary fibroses, or sleep apnoea syndrome (OSAS), pneumonia selected from infectious pneumonia, influenza or avian flu pneumonia, severe acute respiratory syndrome (SARS), or *pneumocystis* pneumonia, infectious diarrhoea selected from *Clostridium difficile* infection, EHEC infection, *salmonella* gastroenteritis, *campylobacter* enteritis, food poisoning by enterotoxin-producing bacteria, cholera, yersinosis, shigellosis, cryptosporidiosis, or listeriosis, food allergies selected from celiac disease, lactose intolerance, or bile salt malabsorption syndrome, inflammatory kidney disorders or others related to dysbiosis of the microbiota selected from urethritis, chronic renal failure, or urolithiasis, multiple sclerosis, lymphangitis, and anorexia, bulimia, depression, bipolar syndrome, autism, schizophrenia, or Tourette syndrome.

12. The method of claim 11, wherein the subject is a human subject or non-human animal.

* * * * *

SEQUENCE LISTING

```
<160> NUMBER OF SEQ ID NOS: 1

<210> SEQ ID NO 1
<211> LENGTH: 1524
<212> TYPE: DNA
<213> ORGANISM: Christensenella minuta

<400> SEQUENCE: 1

agagtttgat cctggctcag gacgaacgct ggcggcgtgc ttaacacatg caagtcgaac     60

gaggttgccc tttgtgaatc cttcgggagg aactgtgggt ataccgagtg gcggacgggt    120

gagtaacgcg tgagcaacct gccctgcaac gggggacaac agttggaaac gactgctaat    180

accgcatgag accacgaaac cgcatggttt tgaggtaaaa ggatttattc gatgcaggat    240

gggctcgcgt cccattagat agttggtgag gtaacggccc accaagtcaa cgatgggtag    300

ccgacctgag agggtgatcg gccacactgg aactgagaca cggtccagac tcctacggga    360

ggcagcagtg gggaatattg ggcaatgggg gaaaccctga cccagcaacg ccgcgtgagg    420

gaagaaggtc ttcggattgt aaacctttgt cctatgggac gaaagaaatg acggtaccat    480

aggaggaagc tccggctaac tacgtgccag cagccgcggt aatacgtagg gagcaagcgt    540

tgtccggaat tactgggcgt aaagggtgcg taggtggtca tgtaagtcag atgtgaaaga    600

ccggggctta accccggggt tgcatttgaa actgtgtgac ttgagtacag gagagggaag    660

tggaattcct agtgtagcgg tgaaatgcgt agatattagg aggaacacca gtggcgaagg    720

cgactttctg gactgtaact gacactgagg cacgaaagcg tggggagcaa acaggattag    780

ataccctggt agtccacgcc gtaaacgatg gatactaggt gtggggcccg atagggttcc    840

gtgccgaagc aaacgcatta agtatcccgc ctggggagta cgatcgcaag gttgaaactc    900
```

-continued

```
aaaggaattg acgggggccc gcacaagcag cggagcatgt ggtttaattc gaagcaacgc    960

gaagaacctt accaaggctt gacatcctct gacgactgta gagatacagt ttcccttcgg   1020

ggcagagaga caggtggtgc atggttgtcg tcagctcgtg tcgtgagatg ttgggttaag   1080

tcccgcaacg agcgcaaccc ttattgctag ttgccagcgc gtaaaggcgg gaactctagt   1140

gagactgccg gggacaactc ggaggaaggt ggggacgacg tcaaatcatc atgcccctta   1200

tgtcttgggc tacacacgtg ctacaatggc cggtacaaag ggcagcgaac ccgtaagggg   1260

aagcgaatct caaaaagccg gtcccagttc ggattgtggg ctgcaacccg cccacatgaa   1320

gtcggagttg ctagtaatcg cgaatcagca tgtcgcggtg aatgcgttcc cgggccttgt   1380

acacaccgcc cgtcacacca cggaagttgg gagcacccga agccagtggc ttaaccgtaa   1440

ggagagagct gtcgaaggtg agatcaatga ctggggtgaa gtcgtaacaa ggtagccgta   1500

tcggaaggtg cggctggatc acct                                          1524
```